United States Patent
Wozniak

(10) Patent No.: US 12,304,164 B2
(45) Date of Patent: May 20, 2025

(54) MATERIAL AND BIOLOGICAL RESPONSE OF FEMTOSECOND PHOTO-MODIFICATION IN HYDROGEL AND CORNEA

(71) Applicant: University of Rochester, Rochester, NY (US)

(72) Inventor: Kaitlin T. Wozniak, Rochester, NY (US)

(73) Assignee: University of Rochester, Rochester, NY (US)

( * ) Notice: Subject to any disclaimer, the term of this patent is extended or adjusted under 35 U.S.C. 154(b) by 108 days.

(21) Appl. No.: 17/779,289

(22) PCT Filed: Nov. 25, 2020

(86) PCT No.: PCT/US2020/062269
§ 371 (c)(1),
(2) Date: May 24, 2022

(87) PCT Pub. No.: WO2021/108585
PCT Pub. Date: Jun. 3, 2021

(65) Prior Publication Data
US 2022/0402227 A1 Dec. 22, 2022

Related U.S. Application Data

(60) Provisional application No. 62/940,066, filed on Nov. 25, 2019.

(51) Int. Cl.
*B29D 11/00* (2006.01)
*B29D 11/02* (2006.01)
*A61L 27/52* (2006.01)

(52) U.S. Cl.
CPC ...... *B29D 11/023* (2013.01); *B29D 11/00355* (2013.01); *B29D 11/00461* (2013.01); *A61L 27/52* (2013.01); *A61L 2430/16* (2013.01)

(58) Field of Classification Search
CPC ............ B29D 11/023; B29D 11/00355; B29D 11/00461
See application file for complete search history.

(56) References Cited

U.S. PATENT DOCUMENTS

| 8,932,352 B2 | 1/2015 | Knox et al. |
| 9,144,491 B2 | 9/2015 | Knox et al. |
| (Continued) | | |

FOREIGN PATENT DOCUMENTS

| WO | 2019010345 A1 | 1/2019 |
| WO | 2020102514 A1 | 5/2020 |

OTHER PUBLICATIONS

Brooks et al. (2014) "Precision large field scanning system for high numerical aperture lenses and application to femtosecond micromachining of ohpthalmic materials." Review of Scientific Instruments 85 (6), 065107.

(Continued)

*Primary Examiner* — Mathieu D Vargot
(74) *Attorney, Agent, or Firm* — Harter, Secrest & Emery LLP; Andrew J. Anderson, Esq.

(57) ABSTRACT

Systems and methods for optimizing laser damage threshold and induced phase change range in a method of writing phase change structures in a hydrogel material with a femtosecond laser writing system focusing a laser beam into the hydrogel material. A laser pulse width and a laser effective NA are selected for a given focused laser average power range to increase the laser damage threshold relative to use of laser pulse widths shorter than the selected laser pulse width and/or use of laser effective NAs greater than the selected laser effective NA. In a particular embodiment, the focused laser average power is from 1 to 5000 mW, the selected laser pulse width is greater than about 165 fs, and the selected laser effective NA is less than 0.50. Applications of the techniques described include laser induced refractive (Continued)

index change (LIRIC) customization of contact lenses, intraocular lenses, and other ophthalmic materials.

19 Claims, 17 Drawing Sheets

(56) References Cited

U.S. PATENT DOCUMENTS

| | | |
|---|---|---|
| 2008/0001320 A1 | 1/2008 | Knox et al. |
| 2009/0143858 A1* | 6/2009 | Knox .................. C08J 7/12 |
| | | 623/6.56 |
| 2012/0310340 A1 | 12/2012 | Knox et al. |
| 2016/0074967 A1 | 3/2016 | Sahler et al. |
| 2022/0001495 A1* | 1/2022 | Knox .................. A61F 2/16 |

OTHER PUBLICATIONS

Brooks, D. (2018). "Design of Intra-Tissue Refractive Index Shaping Systems and Their Implementation in Creating Refractive Structures in Live Cats" University of Rochester, Rochester, NY.
D.E.Savage et al. (2014) "First Demonstration of Ocular Refractive Change Using Blue-IRIS in Live Cats" Investigative ophthalmology & visual science, 55(7), 4603.

* cited by examiner

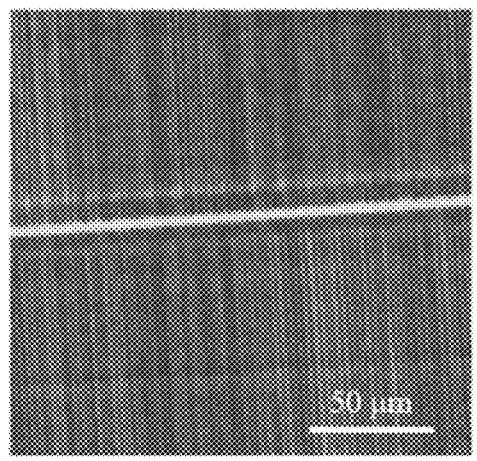
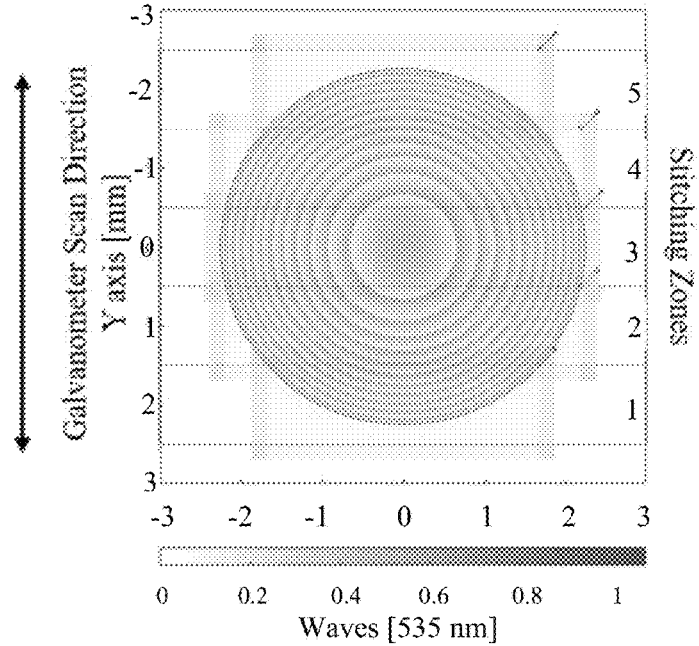
FIG. 17A  FIG. 17B
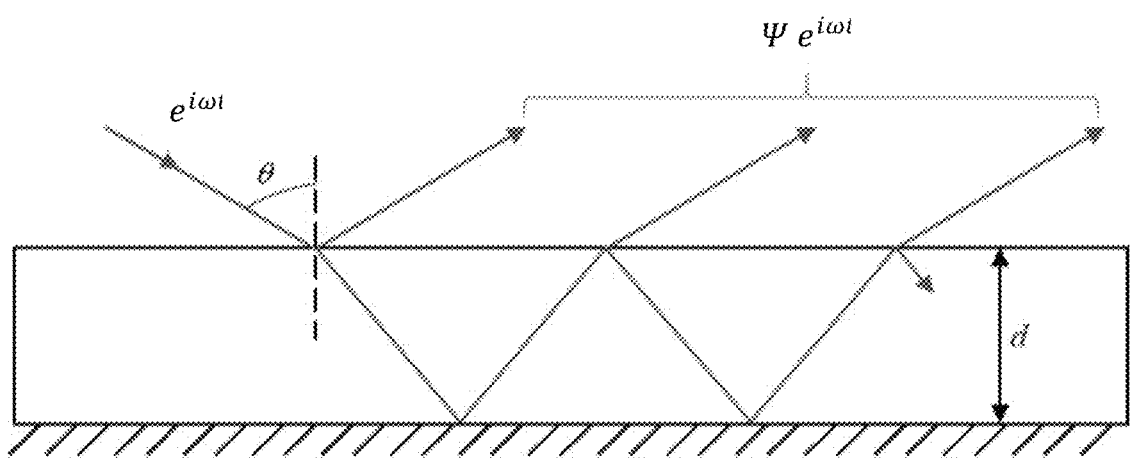
FIG. 18

Interferogram

Phase Map

MATERIAL AND BIOLOGICAL RESPONSE OF FEMTOSECOND PHOTO-MODIFICATION IN HYDROGEL AND CORNEA

RELATED FIELDS

This disclosure is in general directed towards femtosecond micromachining for inducing refractive index (RI) or phase change in hydrogel-based materials and other ophthalmic materials, and more particularly towards modifying the index of refraction of optical polymeric lens materials by a high-repetition, low-pulse energy femtosecond laser.

BACKGROUND

Laser photo-modification technique which induces refractive index (RI) change in transparent ophthalmic materials with the aim of improving human vision was first demonstrated by Ding et al. in hydrogel materials in 2006 and in corneal tissue in 2008. This photo-modification technique can be used to create custom refractive corrections in ophthalmic hydrogels used, e.g., for contact lenses and intraocular lenses (IOLs). In cornea, this procedure represents a non-invasive alternative to traditional laser vision correction procedures such as laser in-situ keratomilcusis (LASIK) or photorefractive keratectomy (PRK). Femtosecond micromachining has been utilized to create highly localized microscopic structures inside materials, including three-dimensional microfabrication within silica glasses, buried tubular waveguides written in bulk poly(methyl methacrylate), and channel waveguides or diffraction gratings formed in cross-linkable PMMA-based copolymers, owing to its unique characteristics, such as rapid and precise energy deposition into the materials, elimination of thermal diffusion to the surrounding area, structural modification within the focal volume, and etcetera. Over the last decade, this technique has been applied to alter the optical properties of ophthalmic materials, such as hydrogel-based contact lenses, intra-ocular lenses (IOL), and cornea tissues, by creating different refractive index shaping structures. Gandara-Montano et al. successfully wrote arbitrary Zernike polynomials in hydrogel-based contact lenses. A phase-wrapped lens was written directly inside an IOL to alter the hydrophilicity of targeted areas, and also high-quality gradient-index (GRIN) Fresnel lenses with wide power range from −3.0 to +1.5 diopters were written in plano contact lens materials. NIR/Blue femtosecond lasers have been used for noninvasive Intra-Tissue Refractive Index Shaping (IRIS) inside corneal tissue and even in the eyes of living cats.

U.S. Publication No. 2008/0001320, the disclosure of which is incorporated herein by reference in its entirety, more particularly describes methods for modifying the refractive index of optical polymeric materials, such as intraocular lenses, corneal inlays, or contact lenses, using very short pulses from a visible or near-IR laser having a pulse energy from, e.g., 0.5 nJ to 1000 nJ, where the intensity of light is sufficient to change the refractive index of the material within the focal volume, whereas portions just outside the focal volume are minimally affected by the laser light. Irradiation within the focal volume results in refractive optical structures characterized by a change in refractive index of 0.005 or more relative to the index of refraction of the bulk (non-irradiated) polymeric material. Under certain irradiation conditions and in certain optical materials, a change in refractive index of 0.06 was measured. The change in refractive index can be used to form patterned desired refractive structures in the optical polymeric material.

U.S. Publication No. 2012/0310340, the disclosure of which is incorporated herein by reference in its entirety, further describes a method for providing changes in refractive power of an optical device made of an optical, polymeric material by forming at least one laser-modified, gradient index (GRIN) layer disposed between an anterior surface and a posterior surface of the device by scanning with light pulses from a visible or near-IR laser along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned.

Such femtosecond laser writing processes have alternatively been referred to as Laser Induced Refractive Index Change (LIRIC), Intra-tissue Refractive Index Shaping (IRIS) in ocular tissues, or correspondingly Intra-Polymer Refractive Index Shaping (IRIS) in optical polymers, such as intraocular lenses, contact lenses or corneal inlays. The term Blue-IRIS has been used to more particularly refer to IRIS performed with blue light, and more particularly with wavelength of around 400-405 nm. The femtosecond laser writing process may also be referred to as micromachining. For the remainder of this disclosure we will use the term LIRIC as a general term for the femtosecond photo-modification of polymeric materials and ocular tissue.

In such processes, the irradiated regions of the optical material can take the form of two- or three-dimensional, area or volume filled refractive structures. The refractive structures are formed by scanning the laser over a select region of the polymeric material resulting in refractive optical structures that can provide spherical, aspherical, toroidal, or cylindrical correction to a polymeric lens. In fact, any optical structure can be formed to yield positive or negative power corrections. Moreover, the optical structures can be stacked vertically or written in separate planes in the polymeric material to act as a single lens element.

There are many factors that can determine the effectiveness of a laser-induced refractive index change (LIRIC), including both material properties and laser exposure parameters. Material properties including chemical composition, water content, dopant type or dopant concentration have been studied so as to extend the limit of maximum achievable refractive index change.

The Raman spectrum signature arising from O—H stretching vibration of water centered at 3420 $cm^{-1}$ shows that larger phase change is associated with higher water content in the modified region and the lower refractive index of water compared to the studied hydrogels may account for the negative phase change induced in the laser-treated area. The function of water in the femtosecond micromachining process has been considered as increasing the heat-induced breakdown threshold due to the high heat capacity, slowing down the heat dissipation from the laser-treated area into the surrounding due to low heat diffusivity, or facilitating the photo-induced hydrolysis of polymeric materials in aqueous media.

As for the chemical composition needed for at least some femtosecond writings, there are two active components, a dopant and a quencher, to increase the energy deposited via nonlinear absorption and to transfer the energy absorbed for the chemical reaction to take place. Doped hydrogels have been reported to produce much larger RI change than undoped hydrogels because of enhanced nonlinearity absorption coefficient.

Apart from material properties, the induced RI change is also highly dependent on the system parameters and the effects of many system parameters, such as the scan speed, the laser average power, the numerical aperture (NA), the pulse width, the laser beam wavelength, and the number of layers written in the same area. Many of these parameters have been widely studied so as to optimize the femtosecond micromachining process. It has been reported that larger refractive index change can be induced in hydrogel polymers with a lower scan speed, a higher average power, and a shorter laser wavelength.

While progress has been made in the past studying factors that impact the effectiveness of the laser-induced refractive index change (LIRIC) in some materials, there remains room for improvement.

SUMMARY

This disclosure describes systems and methods for optimizing laser damage threshold and induced phase change range in a method of writing phase change structures in a hydrogel material with a femtosecond laser writing system focusing a laser beam into the hydrogel material, comprising selecting a laser pulse width and a laser effective NA for a given focused laser average power range to increase the laser damage threshold relative to use of laser pulse widths shorter than the selected laser pulse width and/or use of laser effective NAs greater than the selected laser effective NA. Applications of the techniques described in this patent include LIRIC customization of contact lenses, intra-ocular lenses, and other ophthalmic materials.

In a particular embodiment, the focused laser average power is from 1 to 5000 mW, the selected laser pulse width is greater than about 165 fs, and the selected laser effective NA is less than 0.50.

In some embodiments, the selected laser pulse width is greater than or equal to about 180 fs, greater than or equal to about 200 fs, greater than or equal to about 210 fs, greater than or equal to about 250 fs, greater than or equal to about 300 fs, or greater than or equal to about 350 fs.

In some embodiments, the selected laser pulse width is less than or equal to about 500 fs, or less than or equal to about 400 fs.

In some embodiments, the selected laser effective NA is less than or equal to about 0.49, less than or equal to about 0.4, less than or equal to about 0.3, less than or equal to about 0.26, less than or equal to about 0.25, less than or equal to about 0.20, or less than or equal to about 0.19.

In some embodiments, the selected laser effective NA is greater than or equal to about 0.05, or greater than or equal to about 0.1.

In some embodiments, the focused laser has a wavelength in the visible or near-IR range, and in more particular embodiments may be in the range of 515 nm to 520 nm, or 1030 nm to 1040 nm, or 400 nm to 410 nm, or 800 nm to 810 nm.

Further embodiments may comprise the further step of writing a desired phase change pattern in a hydrogel material with the femtosecond laser writing system at the selected laser pulse width and selected laser effective NA for the given focused laser average power range by scanning the pulsed focused laser beam relative to the hydrogel material to write one or more refractive index changes into the hydrogel material.

In additional embodiments of the disclosure, a laser writing system for modifying a hydrogel material is described, the laser writing system comprising: a laser configured to generate a laser beam; and a laser writing head configured to focus and direct the laser beam to the hydrogel material to write one or more localized refractive index modifications into the hydrogel material; wherein the laser writing system is configured to have a laser pulse width and laser effective NA selected in accordance with the disclosed methods.

In some embodiments, the system is configured to generate a focused laser beam having a wavelength in the visible or near-IR range, and in more particular embodiments a wavelength in the range of 515 nm to 520 nm, or 1030 nm to 1040 nm, or 400 nm to 410 nm, or 800 nm to 810 nm.

In some embodiments, the hydrogel material is an ophthalmic device selected from contact lenses, intraocular lenses, or corneal implants.

BRIEF DESCRIPTION OF THE DRAWINGS

FIG. 17A: DIC micrograph of the intersection between two stitching zones and FIG. 17B: Schematic of a 5 mm Fresnel lens created using the galvanometer scanning system and stitching techniques. Light gray rectangular areas represent GY scan regions. Circular areas represent areas of controlled laser exposure and corresponding gradient phase change.

FIG. 18: Diagram of the reflectance of a Gires-Tournois Interferometer mirror. The complex amplitude, $\Psi$, contains a phase delay to the incident plane wave which is dependent on the angle of incidence and the thickness of the mirror.

DETAILED DESCRIPTION

The following detailed description sets out examples of LIRIC writing systems and methods for ophthalmic materials, as well as techniques for improving LIRIC manufacturing systems and methods. The specific examples described below are for illustrative purposes only, and are not intended to limit the scope of the inventions. Changes could be made to the systems, methods, and techniques described below without departing from the scope or spirit of the inventions.

LIRIC Experimental Systems and Metrology Devices

The development of LIRIC as a technique for inscribing GRIN lenses in ophthalmic hydrogel and corneal tissue with the goal of improving human vision has been an incremental process, spanning over a decade. The primary goal of the continued improvement and development of LIRIC systems has been to reach clinically relevant parameters. LIRIC preferably should be capable of inscribing large, corneal-sized GRIN patterns with large refractive changes in less than 5 minutes.

Figure 1:
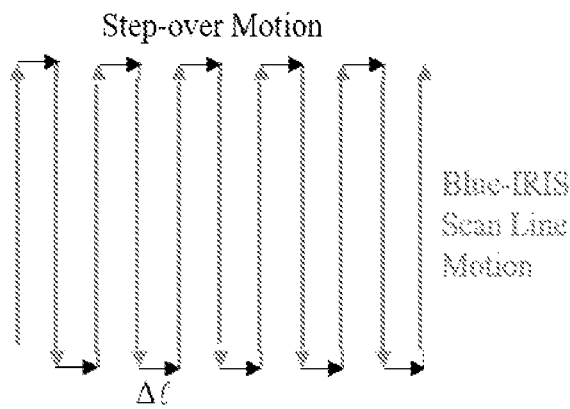
FIG. 1: Raster scan pattern used for inscribing LIRIC GRIN lines. Written lines are separated by the step-over motion, controlled by an orthogonal linear stage. The laser power is set to zero during the step-over to prevent damage to the sample. The distance between adjacent lines is called the line spacing and is represented by $\Delta l$.
Figure 2:
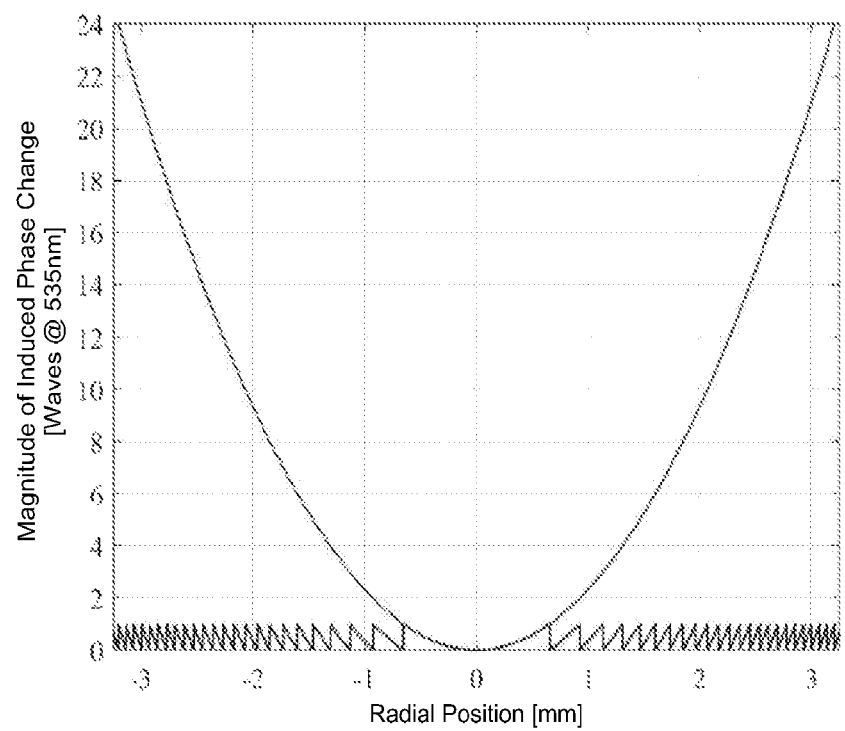
FIG. 2: Comparison of a standard phase profile and a Fresnel lens for a 2.5 D lens over a 6.5 mm diameter region with a design wavelength of 535 nm.

Initial systems utilized XYZ stages that slowly translated a sample beneath the focusing microscope objective to obtain small magnitude RI change. In order to achieve clinical relevance, a LIRIC system must be capable of inscribing large area GRIN patterns. The writing time for a large area pattern is dependent on several factors. Since the sample or the objective is translated using linear stages, a raster scan pattern is used to cover large areas (FIG. 1). The writing time is dependent on the speeds of two linear stages, the stage along the scan direction and the stage controlling the step-over between individual GRIN lines.

An additional limitation is the velocity profile of the linear stage along the scan direction. The nonlinear RI change is an exposure-based interaction which depends on the laser power density and the laser dwell time, which is determined by the linear stage's velocity profile. A uniform velocity profile is required to achieve precise control of the RI change within the sample. A non-uniform LIRIC pattern can result in RI irregularities that cause scattering effects. This would degrade the optical performance of LIRIC refractive correctors.

The multiphoton nature of the process necessitates high peak powers and tight focus within the sample. A microscope with a high numerical aperture (NA) is needed to achieve a tight focus wherein the peak power is high enough to induce RI change. This reduces the spot size of the laser, and therefore, the laser-material interaction region as well. The line spacing of the raster scan pattern ($\Delta$ 1 in FIG. 1) must on the same order as the spot size (~0.5-1.5 μm), necessitating high precision step over stages. If the overlap of adjacent scan lines is too small or non-existent, the induced RI change may act as a diffraction grating, creating spurious scattering effects which degrade optical performance. If the GRIN lines are too closely overlapped, the accumulated effects of the laser interaction may result in damage in the material. This interaction between NA and line spacing is called the fill factor and is defined as the percent overlap between adjacent lines.

Aside from the motion control considerations, there are several important optical concerns that must be addressed to maximize the efficacy of LIRIC. The peak power of a pulsed laser is determined by the pulse width, repetition rate, and average power of the laser. The pulse width in the focal region is not the same as the pulse width exiting the laser. Dispersion from the optical elements used to route the laser beam through the system will stretch the pulse temporally. Therefore, dispersion compensation is a necessary part of an optimized LIRIC system. Because the RI change is highly localized due to the multiphoton nature of the process, the average power of the laser must be carefully controlled in order to modulate the RI appropriate to create GRIN patterns. A further consideration with respect to average power comes from power loss through the optical system, primarily due to Fresnel reflections or absorption. Specifically, when working at 400 nm, optical components with the highest transmission should be chosen to minimize loss. The microscope objective, dispersion compensation elements, and intensity control elements have the greatest impact on laser power attenuation. Finally, the repetition rate of the laser is determined by the type of laser used to generate the femtosecond pulses. A Ti:Sapphire laser oscillator with a repetition rate of 80 MHz to 93 MHz, e.g., has been employed.

Mechanical improvements have been undertaken to ensure that LIRIC patterns can cover a 6.5 mm optical zone. However, RI change must be maximized as well. In terms of refractive corrections, it is more practical to discuss the accumulated optical phase of a wavefront, rather than RI change. The relationship between phase and RI is given by $$\Delta\varphi=[2\pi b\Delta n]/\lambda \qquad (2.1)$$

where $\Delta\varphi$ is the induced phase, b is the thickness of the region of RI change, $\Delta n$ is the magnitude of RI change, and $\lambda$ is the measurement wavelength of the induced phase. The thickness of a LIRIC structure can be estimated through differential contrast microscopy, and tends to be on the order <10 μm. This means LIRIC patterns may be approximated as a thin lens.

One of the most common refractive prescriptions is -2.5 D to treat myopia. Using a design wavelength of 535 nm (the center of the visual spectrum), a 2.5 D lens over a 6.5 mm optical zone can be calculated to require a maximum phase change of 24.67 waves at 535 nm. This magnitude of phase change is significantly larger than LIRIC is capable of producing. In fact, using Equation (2.1) yields a maximum RI change of 0.7, an unfeasible magnitude of change.

Instead of a purely refractive structure, it is instead possible to use phase wrapping techniques to create a structure known as a Fresnel lens, also called a kinoform lens. By wrapping the phase at 1 wave intervals, it is possible to reduce the necessary phase change to 1 wave and maintain the optical power. Fresnel lenses are commonly used in intraocular lenses. They are a useful optical device for several reasons. As stated above, the ability to collapse the phase profile reduces the necessary phase needed to create a powerful lenses. Secondly, Fresnel lenses work as a diffractive optical element. As with all diffractive elements, the spacing between periodic structures and the amplitude of those structures are critical parameters. For Fresnel lenses, the number of Fresnel zones determines the focus. In two Fresnel lenses of the same diameter, the lens with more zones will be the more powerful lens. Furthermore, if the magnitude of phase change at the peak of the Fresnel zones is not exactly one wave, then some of the incident light will be diffracted into other orders. A perfect Fresnel lens will only diffract into the first order and therefore be monofocal.

Three systems which have been used for LIRIC experiments, as well as their limitations, will now be described. Table 1 shows several of the key parameters for each system. The scanning modalities listed are for the LIRIC scanning direction. All systems also include linear stages for creating raster scan patterns. All numerical apertures are for water immersion objectives. The NA for System 1 was not measured at the time of the experiment; therefore the nominal NA of the microscope objective is listed. All systems had a nominal pulse width of 100 fs, but only Systems 2 and 3 employed pulse compression subsystems to compensate for native group dispersion in the system.

TABLE 1

LIRIC system parameters.

| System | Wavelength [nm] | Scanning Modality | NA | Max Average Power [mW] |
|---|---|---|---|---|
| System 1 | 400 | Vibration Exciter | ~1.0 nominal | 60 |
| System 2 | 400 | Flexure | 0.23-0.74 | 300 |
| System 3 | 405 | Galvanometer | 0.19-0.49 | 275 |

System 1: Commercial Vibration Exciter

Figure 3:
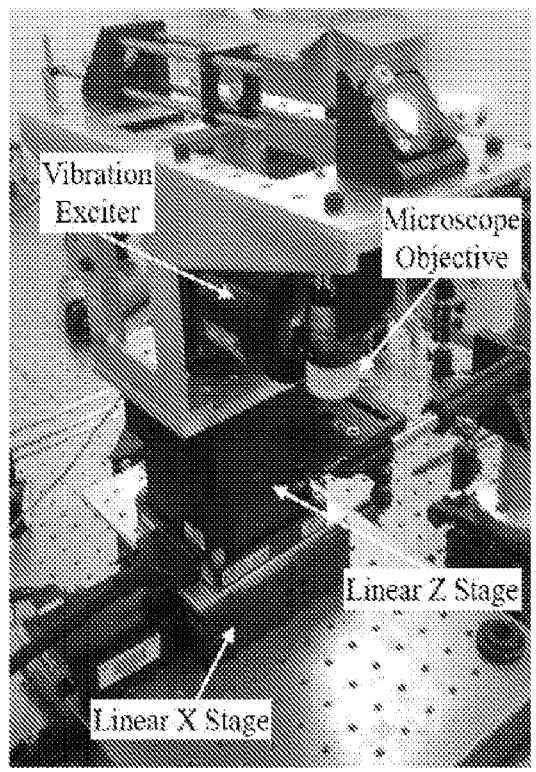
FIG. 3: Photograph of the commercial vibration exciter system. The vibration exciter will translate the focal volume of the laser through the sample, creating LIRIC GRIN lines. The linear X stage is used for the slow axis step-over motion to create adjacent lines in a raster scan pattern. The Z stage is used to position the focal volume within the sample. [Adapted from Brooks et al. (2014). Review of Scientific Instruments. 85 (6): p. 065107].

System 1 was the first prototype system for in vivo corneal writing. The system was used for the first in vivo LIRIC experiments (D. E. Savage et al., Investigative ophthalmology & visual science, 55 (7), 4603 (2014)). Until its design and construction, all previous LIRIC systems had fixed beam paths and used XYZ linear stages to translate the sample beneath the stationary microscope objective. Brooks and Savage designed a new prototype system which consisted of a commercial vibration exciter (Brüel & Kjær Measurement Exciter Type 4810) that translated the microscope objective in the +Y direction over the stationary sample. The microscope objective was mounted to the vibration exciter using a mounting ring that was custom machined to hold it (FIG. 3). A linear translation stage (Newport GTS70) was used for the slow axis, step-over motion. Finally, a Newport GTS30V was used as the Z-axis stage to position the focal volume in the sample.

Also shown in FIG. 3 are the final elements of the beam steering subsystem. This consists of two fold mirrors per mechanical axis mounted to a custom mounting plate. When aligning a laser system to with multiple degrees of freedom, it is vital that the laser be parallel to each axis individually. If this is not the case, the laser beam would become misaligned and not reach the microscope objective appropriately as the stages moved. To achieve this, the beam line was aligned using two tip-tilt fold mirrors per axis. This allowed for four degrees of freedom for alignment, two per mirror, for each axis that would move during the LIRIC procedure. The final element of the beam steering system is a prism which steered the beam into the objective through total internal reflection. The prism was attached to a custom threaded mount which screwed into the top of the objective.

Figure 4:
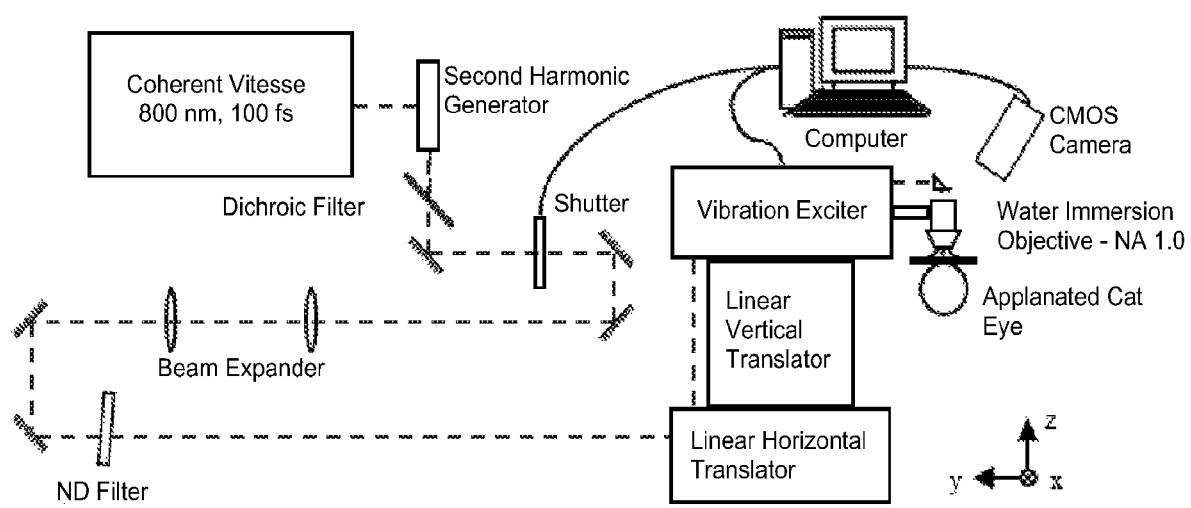
FIG. 4: Diagram of LIRIC System 1. An 800 nm, 100 fs laser is frequency doubled to produce 400 nm laser pulses which are tightly focused through a 1.0 NA, water immersion objective. The microscope objective is mounted to a commercial vibration exciter which, in concert with a linear horizontal stage, raster scans the laser focal volume across a 2.5 mm by 2.5 mm area, creating a GRIN lens.

A diagram of the optical system of System 1 is shown in FIG. 4. A second harmonic generation (SHG) is used to frequency double the light produced from a Ti:Sapphire oscillator (Vitesse; Coherent Corporation). This mode-locked laser emitted 800 nm, 100 fs pulses with a repetition rate of 80 MHz. After SHG, the system produced ~250 mW of 400 nm light, which was then passed through a dichroic filter to remove any spurious 800 nm light. Then, the beam was routed through a Galilean style beam expander to increase the diameter of the beam in order to fill the entrance pupil diameter of the microscope objective (20×, W Plan-Apochoromat, Carl Zeiss). The objective had a nominal NA of 1.0 with water immersion. A metallic, variable neutral density filter was used to attenuate the beam's average power to 60±1 mW, which corresponds to energies on the order to 0.8 nJ, below the damage threshold of cornea.

System 2: Flexure-Based Scanner

A custom flexure-based design was created to improve the velocity profile, increase the maximum stroke for LIRIC patterns to a clinically-relevant size, implement active laser intensity control, and improve the geometry of the laser delivery system for ease of use during in vivo studies (D. R. Brooks et al., Precision large field scanning system for high numerical aperture lenses and application to femtosecond micromachining of ophthalmic materials, *Review of Scientific Instruments*, 85 (6), 065107 (2014). The basic optical system of the instrumentation remained largely unchanged from System 1. Most improvements to this system were of a mechanical nature, focused in the scanning system and laser delivery subsystem. However, a few optical improvements were instituted as well, namely dispersion compensation and an adjustable beam expander.

The main design considerations which drove the development of a custom flexure design were LIRIC writing area and time. As mentioned previously, a clinically relevant optical zone is needed for vision correction. A desired area is 6.5 mm. However, due to the nature of the scanning system, the flexure's stroke must be at least 8 mm to accommodate the turn around where the velocity drops to zero. The writing time is dictated by two main factors: fill factor and scan speed. The fill factor is determined by the effective NA of the system and the line spacing. A high enough fill factor is needed such that adjacent lines overlap a sufficient amount to create a uniform structure. A non-uniform GRIN structure could cause spurious scattering effects, negatively impacting the optical quality of LIRIC structures. To minimize writing time, the flexure's scan speed must be maximized.

Figure 5:
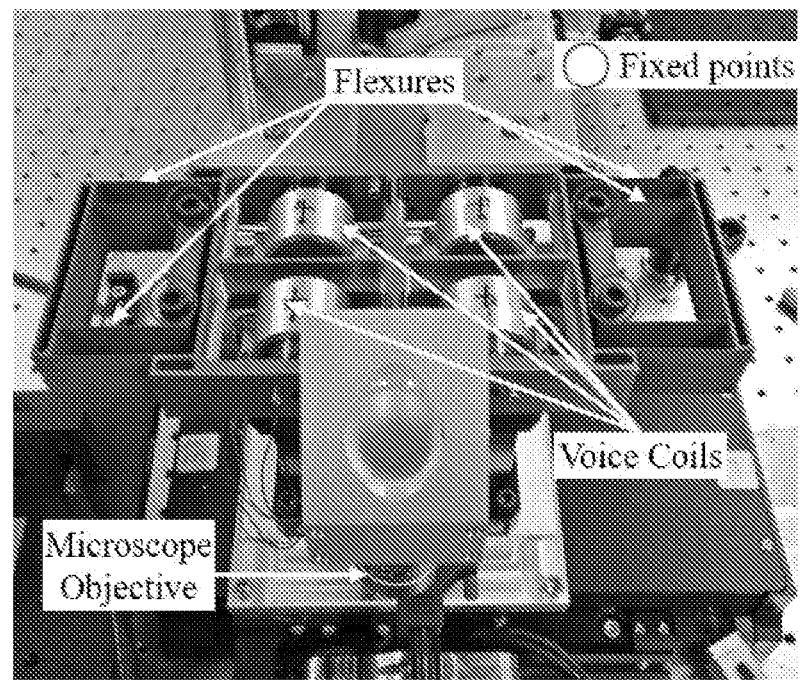
FIG. 5: Photograph of the flexure scanning system. Four voice coils were used to drive a folded parallelogram architecture flexure system. The circles on the inner flexures mark the fixed points, with the moving carriage surrounding the voice coils. The microscope objective was mounted to the front of the moving carriage with the laser beam path passing over the carriage. The beam was then routed into the microscope objective via a folding mirror.

The finalized flexure design is shown in FIG. 5. A folded parallelogram design was chosen to minimize the footprint and aid in ease of mounting. The microscope objective was attached to the front of the flexure, with the laser beam path routed over the top of the moving carriage to a folding mirror which then directed the beam into the microscope objective. A counterweight (not labeled in FIG. 5) was attached opposite the microscope on the moving carriage to limit the excitation of unwanted resonant modes that may arise from an asymmetric weight distribution on the carriage.

Figure 6:
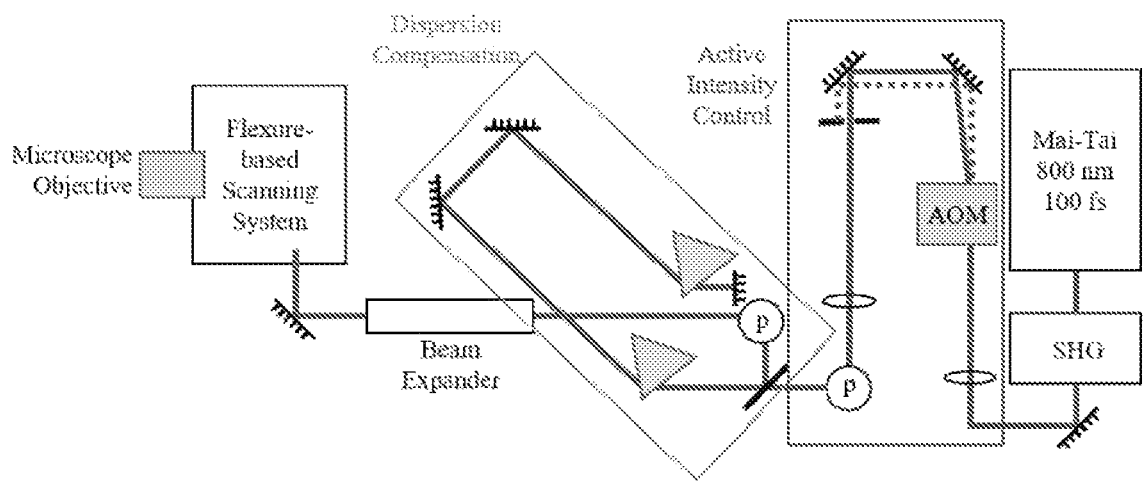
FIG. 6: Optical diagram of LIRIC System 2. A Ti:Sapphire oscillator produces 800 nm, 100 fs pulse train which then was frequency doubled to 400 nm with second harmonic generation. This light was focused into an AOM for laser intensity control in real time. The light was recollimated before entering a dispersion compensation subsystem which used two F2 prisms in a double pass configuration. Then, the light passed through a beam expander and was delivered to the flexure-based scanning system. This system enabled 3D scanning of the focal volume of the 1.0-NA water immersion microscope objective within a stationary sample for the creation of LIRIC GRIN patterns.

As with the previous vibration exciter design, the flexure-based scanning system was mounted on two linear stages: an X-stage responsible for the slow step over, and a Z-stage to correctly position the sample beneath the objective. The final, complete system design is shown in FIG. 6. Unlike the previous system, System 2 incorporated active laser intensity control, dispersion compensation, and a variable beam expander to control NA. Another major difference was the laser used. Previous experiments were performed using a low power Vitesse Ti:Sapphire oscillator from Coherent. With the faster scan speeds achievable by System 2, more laser power was needed to maintain large induced RI change. Therefore, the flexure-based system moved to a Mai Tai HP from Spectra-Physics. The Mai Tai was capable of producing 2.9 W of 800 nm, 100 fs pulses at an 80 MHz repetition rate. In comparison, the Vitesse was only capable of producing ~1 W.

Laser Intensity Control

In System 1, passive laser intensity control was employed to maintain a single average laser power. To modulate induced. RI change, the varying speed of the shaker during its stroke was used to create cylindrical GRIN structures. LIRIC is a multiphoton process, meaning the induced RI change is an exposure-dependent variable. The velocity of the laser, and hence dwell time, coupled with the average power within the focal volume control the magnitude of RI change. The average laser power can be controlled more quickly and precisely than the speed of the flexure's stroke. Therefore, active laser intensity control was employed to precisely modulate induced RI change over large areas. An acousto-optic modulator (AOM) was employed for this purpose due to its rapid rise time. The rise time is defined as the time it takes the acoustic power to change across the active aperture.

There were several considerations for choosing an appropriate AOM for this system. Firstly, the AOM needed a high transmission at 400 nm. Many AOMs have interactive materials, such as tellurium dioxide, which have high absorption in the UV. Even appropriate anti-reflection coatings cannot adequately compensate for the native material's absorption. For LIRIC, a high average laser power is necessary to achieve large magnitude RI change. Furthermore, this absorption could cause thermal lensing of the focused 400 nm beam which would greatly degrade the spot quality of the laser, and therefore the efficacy of LIRIC. Therefore, we deemed an AOM with >90% transmission when no acoustic signal was applied was necessary. Another factor which could reduce efficacy of LIRIC was the dispersion of the AOM. If the pulse is greatly lengthened, the peak power in the focal region is reduced.

The best option for an AOM for the flexure-based system was the M1133-aQ80L-1.5 from Isomet Corp. Appropriate coatings were applied for use at 400 nm, and with no acoustic signal present, the transmission through the AOM was 89%. When an acoustic signal was applied, the transmission into the diffracted 1st order was 72%, which was deemed sufficient for our use. No thermal lensing was observed. The chosen AOM had a rise time of 114 ns across a 1.5 mm active aperture. The separation between the undiffracted light and the ±1 diffracted orders was 7.57 mrad, as determined by the wavelength of the acoustic wave. Finally, this AOM had low dispersion since the interactive medium was quartz, making it the best candidate for System 2. The AOM was controlled with a 0-1 V analog voltage signal which the AOM driver converted into the electronic signal needed to drive the transducer. By adjusting the applied voltage, and thereby the acoustic power of the acoustic wave, it was possible to control the power ratio of the 0th and 1st order diffracted light.

Figure 7:
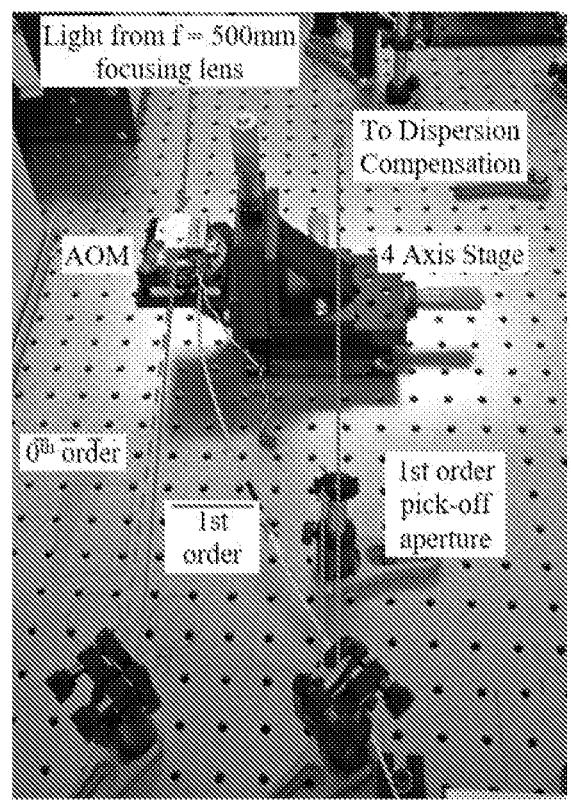
FIG. 7: Beam path through the laser intensity subsystem. The light was focused onto the AOM at the Bragg angle to maximize diffraction efficiency into the first order. To ensure light enters at the Bragg angle, the AOM was mounted to a 4-axis stage with two degrees of rotational freedom and three degrees of translational. A pinhole was used to pick off the 1st order beam which was then recollimated before entering the dispersion compensation subsystem.

Ideally, all light entering the AOM should be either undiffracted or diffracted into the first order to preserve maximum laser intensity. However, in practice, some light is lost to higher order diffraction because there is a small deviation in incident angle due to the nominal divergence of the laser. To overcome this loss, a focusing lens was used to focus the incident beam onto the AOM. After leaving the AOM, a pinhole was used to pick-off only the first order beam. Because the first order diffraction efficiency is highly dependent on the incident angle of the laser, the AOM was mounted to a four axis stage consisting of a rotational mount and a 3 axis translational stage. By placing a power meter after the pinhole and adjusting the four axis mount, it was possible to maximize the intensity of light in the first order diffracted beam. Finally, the beam was recollimated before entering the pulse compression subsystem. The final setup of the laser intensity control subsystem is shown in FIG. 7.

Dispersion Compensation

After exiting the AOM, the laser beam was recollimated before entering the dispersion compensation subsystem. This subsystem played a part in increasing the efficacy of LIRIC. In any optical system, when a pulsed laser travels through optical elements, the pulses experience dispersion, which leads to pulse broadening. The efficiency of femtosecond photo-modification depends on the peak power in the focal volume, which is inversely proportional to the pulse duration. Therefore, by implementing pulse compression techniques, the pulses could remain as short as possible and lower average powers would be needed to achieve large magnitude RI changes. The SHG, AOM, and microscope objective will greatly lengthen the nominal 100 fs due to their large group delay dispersion (GDD) at 400 nm.

When light travels through a dispersive material, the electric field of the wave can be expressed by $$E(t, z) = A\left[t - \left(\frac{z}{v_g}\right)\right]e^{i(\omega t - kz)}, \quad (2.7)$$

where A is the pulse amplitude, vg is the group velocity of the wave, ω is the central frequency of the pulse, and k is the angular wavenumber. The angular wavenumber of pulsed light is a function of frequency due to the broadband nature of the pulses and is given by k(ω)=2ωn/>λ(ω) where n is the index of refraction and λ is the wavelength. The group velocity is given by $$v_g = \frac{d\omega}{dk}. \quad (2.8)$$

Then, the time delay a pulse experiences travelling through a dispersive medium of length L is given by $$\tau_g = \frac{L}{v_g} = L\left(\frac{d\omega}{dk}\right). \qquad (2.9)$$

Now consider a pulse with a bandwidth of $\Delta\omega$. Different spectral regions of the pulse will travel through dispersive media with different group velocities. Therefore, the pulse broadens as it propagates. The broadening of a pulse with bandwidth $\Delta\omega$ will be given by approximately the difference between the fastest and slowest spectral components. From Equation (2.9), it can be shown that the broadening of a pulse due to dispersion can be approximated by $$\Delta \tau_g = L\left(\frac{d^2 k}{d\omega^2}\right)\Delta\omega = L(GVD)\Delta\omega. \qquad (2.10)$$

The group velocity dispersion (GVD) is defined as the second derivative of the angular wavenumber with respect to optical frequency. The magnitude of the GVD gives the pulse broadening per unit bandwidth and per unit length of dispersive material and has units of $fs^2/mm$. Or, the GVD is the GDD per unit length of dispersive material.

To predict the total pulse broadening in System 2, the GDD of each individual element was summed together. In some cases, the GDD was calculated. To do so, the GVD was calculated and multiplied by the thickness of the material. To calculate GVD, the expressions for k and $\omega$ in terms of the speed of light, c, and the wavelength of light were substituted into Equation (2.10). Then, $$GDD = GVD \cdot L = \frac{\lambda^3}{2\pi c^2}\left(\frac{d^2 n}{d\lambda^2}\right)L. \qquad (2.11)$$

Given the sum of the system's GDD, the final pulse width through the system can be found by using $$\tau_f = \frac{\sqrt{\tau_0^4 + 16(\ln 2)^2 \cdot GDD^2}}{\tau_0}, \qquad (2.12)$$

where $\tau_f$ is the final pulse width through the system and $\tau_0$ is the starting pulse width.

The goal of the dispersion compensation subsystem was to get the system's GDD as close to zero as possible, such that the final pulse width approached the nominal 100 fs.

Figure 8:
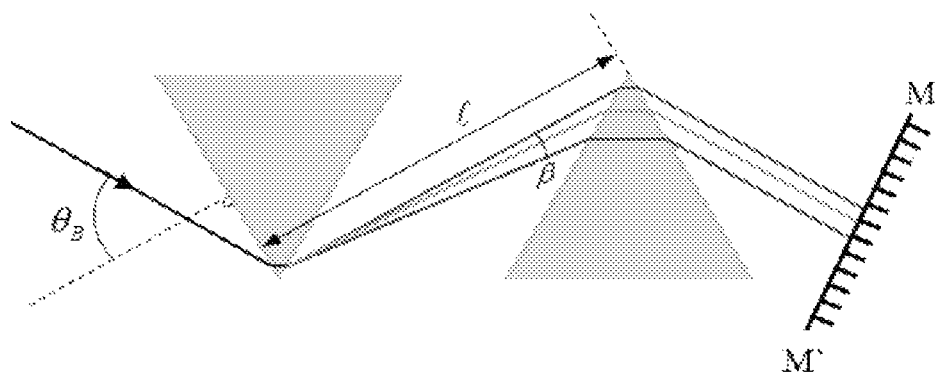
FIG. 8: Diagram of a double pass prism dispersion compensator. Light enters the first prism at Brewster's angle, $\theta_B$, to minimize Fresnel reflections. This is also the angle of minimum deviation for the prisms. The frequency components of the light are separated by the first prism with the angular separation $\beta$. The prisms are separated by distance l, and the configuration is symmetric about the plane MM'. By placing a mirror at plane MM', the system becomes a double pass configuration.

Most optical elements have a positive GDD, where $$\frac{d^2 n}{d\lambda^2} > 0.$$

by introducing optical elements with negative dispersion, the GDD of the system can be reduced. One of the most common methods for introducing negative GDD is to pass the pulse train through a pair of prisms which introduce negative dispersion in the form of angular dispersion. A diagram of the prism configuration is shown in FIG. 8.

The GDD of the prism system is given by $$GDD_{prisms} = \frac{2\ell\lambda^3}{\pi c^2}\left(\left[\frac{d^2 n}{d\lambda^2} + \left(2n - \frac{1}{n^3}\right)\left(\frac{dn}{d\lambda}\right)^2\right]\sin\beta - 2\left(\frac{dn}{d\lambda}\right)^2\cos\beta\right), \qquad (2.13)$$

where l is the prism separation, c is the speed of light in vacuum, $\lambda$ is the wavelength of light, n is the refractive index of the prisms at wavelength $\lambda$, and is $\beta$ is the angular separation of the frequency components of the laser pulse after passing through a single prism. To minimize Fresnel reflections, light is incident on the prisms at Brewster's angle, which is given by $$\theta_B = \arctan\left(\frac{n_2}{n_1}\right) \qquad (2.14)$$

where n2 is the index of refraction of the prisms and n1 is the index of refraction of air. In practice, the prisms' geometry is such that Brewster's angle is also the angle of minimum deviation. In a prism, the angle of minimum deviation is that at which incident and exiting rays form equal angles with the prism faces.

Figure 9:
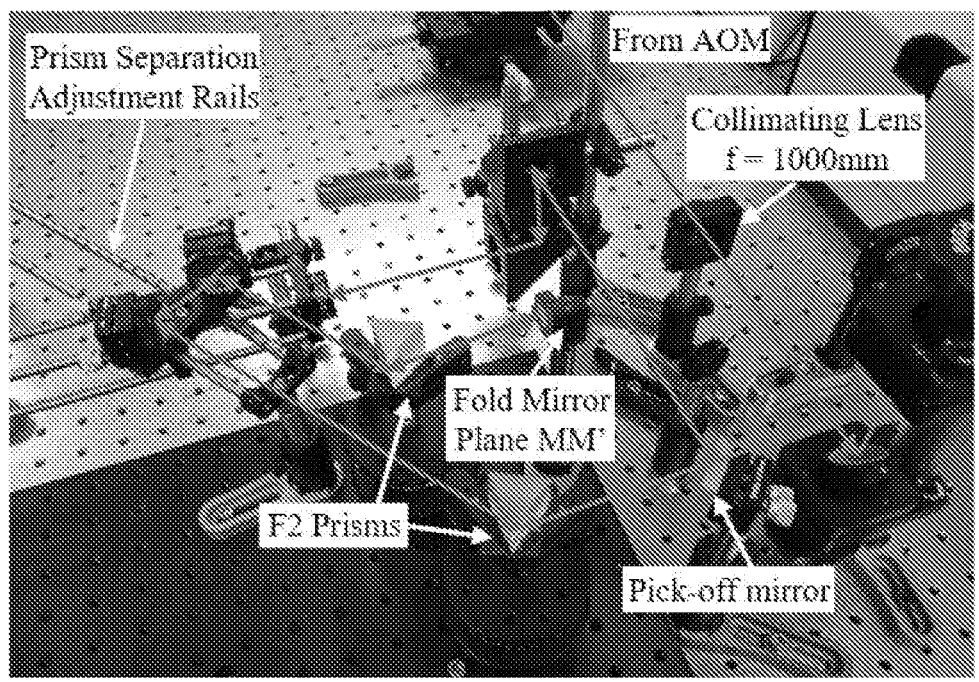
FIG. 9: Beam path through the dispersion compensation subsystem. The beam was collimated before entering the first prism. The prism separation was controlled by two 45° fold mirrors mounted on a rail carriage. A fold mirror in the symmetry plane MM' created a double pass configuration. After the second pass, the returning, compensated beam was picked off with a half mirror and routed to the beam expander.

Several possible prism materials were investigated. Two major considerations factored into the choice. First, the material must have low absorption at 400 nm to ensure minimal power loss and to avoid thermal lensing. Second, the prism separation distance must be practical. Based on this, F2 prisms from Schott were deemed most suitable. After the GDD was estimated for the system, Equation (2.13) was used to find the approximate separation of the prisms. However, due to approximations needed to find the system's GDD, further adjustments of the prism configuration would be needed. For this reason, two fold mirrors were mounted on a rail carriage system, creating an adjustable prism separation. To ensure the angle of incidence was Brewster's angle, the prisms were mounted on rotation stages for precise adjustments. A fold mirror was placed at plane MM' to create a double pass configuration. The dispersion compensation subsystem is shown in FIG. 9.

Figure 10:
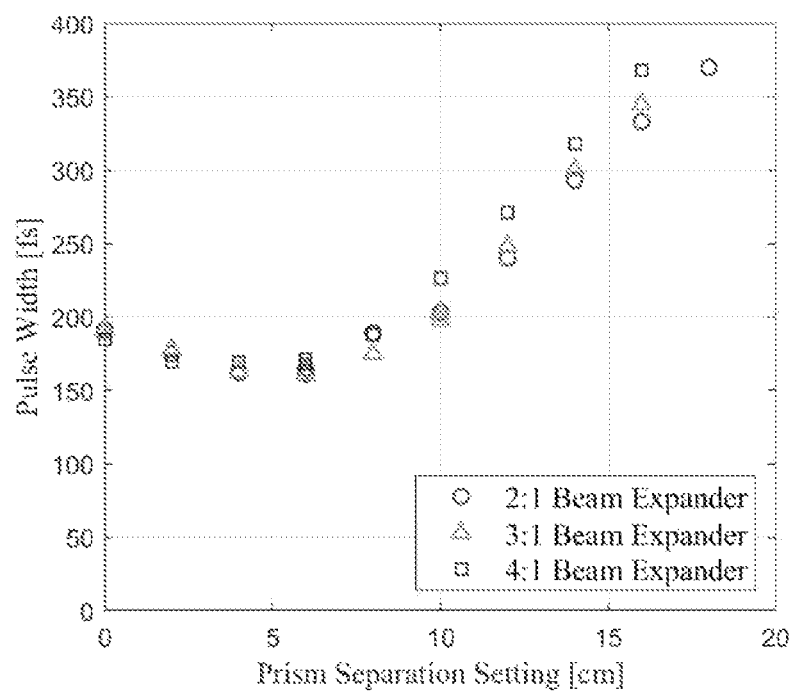
FIG. 10: Pulse width measurements for various prism distance settings. Measured pulse widths were fit to a Gaussian distribution. Measurements were taken with three different beam expander configurations to test varying amounts of dispersion between configurations. There is no significant difference. The minimum pulse width was ~160 fs at a prism separation setting of 4-6 cm.

To validate the dispersion compensation subsystem, pulse widths at various prism separation settings were measured. The two 45° fold mirrors were moved along the carriage rails in 2 cm increments. The beam was passed through the entire system, including the scanning system and the microscope objective. The beam was then recollimated using a fiber coupling lens and routed into an autocorrelator using a fold mirror. The autocorrelator used was a mini TPA (APE, Berlin, Germany). The result from the autocorrelator was fit to a Gaussian distribution. Pulse widths were recorded for three beam expander configurations, to be described in detail in the following section. This was done to ensure the different lenses used in the beam expander configurations did not induce vastly different amounts of dispersion. The pulse measurements for different prism separation settings are shown in FIG. 10. Note, the distance shown is not the actual separation of the prisms, but their location on the carriage rails.

The minimum pulse width was found to be ~160 fs and occurred when the two 45° fold mirrors were located 4 to 6 cm from the end of the rails. The largest pulse width achievable with the carriage rails was 370 fs. In previous LIRIC systems, the pulse width was always set to a minimum to maximize the peak power in the focal volume to increase the magnitude of induced RI change. The effect of longer pulse widths on the efficacy of LIRIC will be discussed below.

800 nm Dispersion Compensation

A co-aligned 800 nm system was built after validation of the 400 nm system. Previous 800 nm systems did not have the high power nor fast scan speeds of System 2. It was a secondary goal to complete a thorough study of NA and pulse width effects at 800 nm using System 2's improved capabilities. To create the co-aligned 800 nm system, a flip mirror was mounted between the Ti:Sapphire laser output and the SHG to re-route the beam to a separate part of the optical bench. There, a second variable dispersion compensation subsystem with CaFl prisms was built before the beam was re-routed back to the 400 nm beam path into the beam expander. All shared mirrors in the system were dual coated for both 800 nm and 400 nm, keeping laser attenuation to a minimum.

Variable NA Beam Expander

Figure 11:
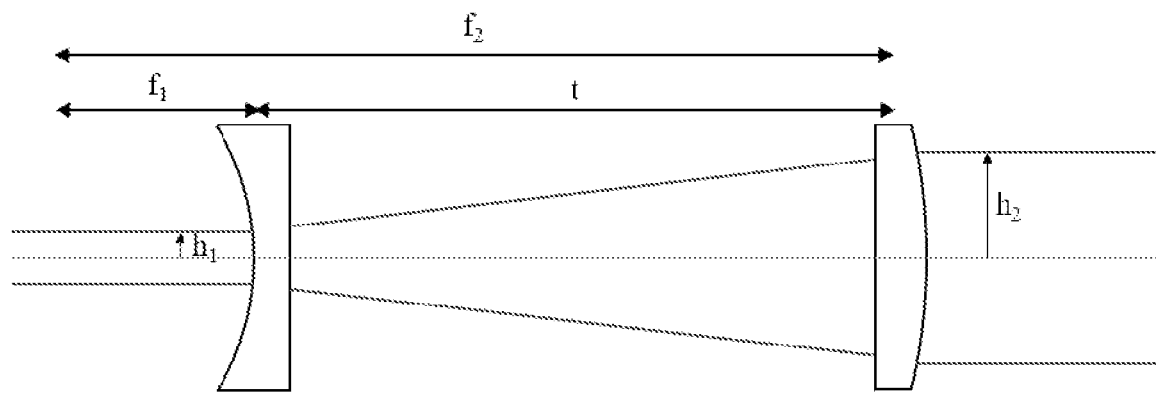
FIG. 11: Diagram of a Galilean beam expander. The negative lens and the positive lens have collocated foci. The separation between the lenses, t, is the sum of the two focal lengths, where fl is negative. The magnification is given by the negative ratio of the two focal lengths.

When exiting the Mai Tai HP, the beam's diameter was 1.2 mm. While travelling through the optical system, that diameter changed little. When exiting the dispersion compensation subsystem, the beam's diameter was roughly the same. However, the microscope objective used in System 2, XLPLN25XWMP2 (Olympus, Tokyo, Japan) had a larger entrance pupil diameter (EPD). Therefore, it was necessary to expand the beam in order to fill the EPD and achieve the full NA of the objective. To do so, a Galilean type beam expander (FIG. 11) was built following the dispersion compensation subsystem.

A Galilean telescope consists of a negative lens followed by a positive lens, with the two foci being collocated. This allows the beam expander to maintain collimation of the beam. The magnification of the beam expander is given by $$M = \frac{h_2}{h_1} = -\frac{f_2}{f_1} \quad (2.15)$$

where M is the magnification, h2 is the exit beam height, h1 is the entrance beam height, f2 is the focal length of the positive lens, and f1 is the focal length of the negative lens. By varying the ratio of the focal lengths, the diameter of the beam may be controlled. This results in control over the working NA of the system.

For System 2, the beam expander was built in a cage system for ease of alignment. Three different beam expanders were used to vary NA in System 2. The focal lengths and magnifications are shown in Table 2.

TABLE 2

The focal lengths and expansion ratios for the three beam expander configurations in System 2.

| F1 [mm] | F2 [mm] | Expansion Ratio |
|---|---|---|
| −100 | 200 | 2:1 |
| −100 | 300 | 3:1 |
| −100 | 400 | 4:1 |

The effective NA was calculated by measuring the beam waist at the EPD using a knife-edge test. A razor blade was attached to a linear translation stage and incrementally translated through the beam at the entrance pupil of the microscope objective. The total travel distance was 20 mm, to ensure the entire beam profile was obtained, and the razor blade moved in increments of 100 μm. In the beam path behind the razor blade the light was collected by a positive lens, f=250 mm, which focused onto a power detector. A typical measurement is shown in FIG. 12.

Figure 12:
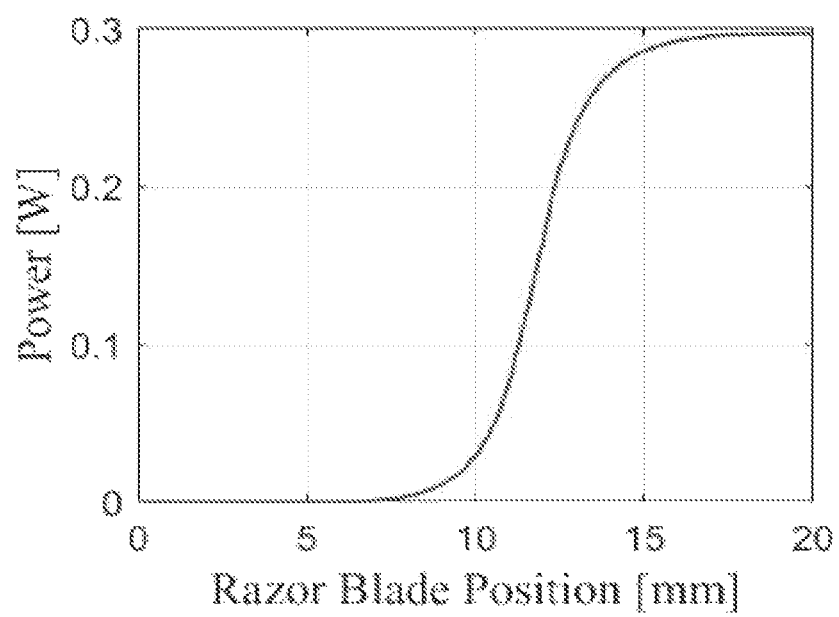
FIG. 12: Example of the results of a knife edge test.

If the beam had a perfectly Gaussian profile, the curve shown in FIG. 12 would be represented by $$P(x) = \frac{P_{tot}}{2}\left[1 - \text{erf}\left(\frac{\sqrt{2}(x - x_o)}{\omega_x}\right)\right], \quad (2.16)$$

where Ptot is the maximum measured power of the laser, x is the position of the razor blade, $x_o$ is the center of the laser beam (defined as where the measure power is half the maximum power), and $\omega_x$ is the $1/e^2$ width of the laser. To calculate the $\omega_x$ of the beam at the EPD, two points are measured from the collected power measurement: where P(x)=10% and 90% of Ptot. This shall be defined as $x_{90-10}$. Comparing this value to the standard Gaussian profile, it can be calculated that $x_{90-10}=1.28\omega_x$. The effective NA is given by $$NA_{eff} = \frac{n\omega_z}{2EFL}, \quad (2.17)$$

where n is the index of refraction in image space, and EFL is the effective focal length of the microscope objective. For System 2, n=1.33 since the microscope objective was water immersion, and EFL=7.2 mm.

Figure 13:
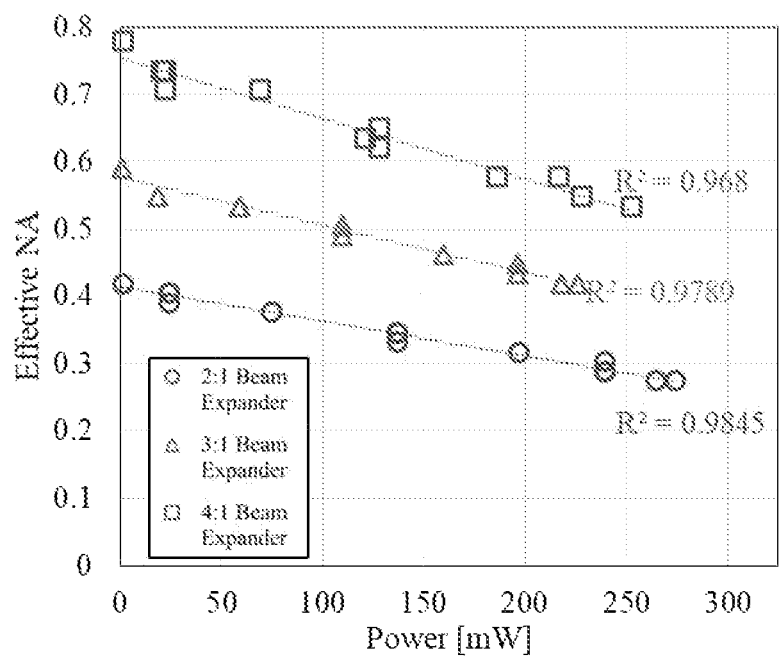
FIG. 13: Results of the knife-edge test to measure effective NA for all three beam expander configurations. Effective NA was power dependent, most likely due to residual thermal bloom in the dispersion compensation prisms. All configurations were measured at three powers and three pulse widths. There was no significant effect of pulse width on effective NA.

It became apparent that the effective NA of the System 2 was power dependent. This was mostly likely from thermal lensing in the dispersion compensation prisms. While F2 was determined to be the best candidate for System 2, it was not ideal. The prisms had an undesirable amount of absorption at 400 nm. However, when compared with other options, they were the only feasible choice. The inverse relationship between NA and power is shown in FIG. 13. The effective NA was measured for all three beam expander configurations at three different power levels as well as at three different pulse widths. Once it was realized that NA varied with laser power, it was deemed prudent to measure if it varied as pulse width and input power. As the pulse width changes, the propagation distance of the laser changes as well, which could possibly decrease thermal lensing at longer propagation distances. However, no significant difference was seen for different pulse widths. Hence, all three pulse widths are plotted together in FIG. 13.

System 2 had a range of effective NA of 0.27 to 0.78. Because the effective NA had a power dependence, all further references to NA in System 2 experiments described herein will refer to the beam expander configuration used. For every power, an effective NA may be calculated given the linear fits from the data shown in FIG. 13.

System 2 improved on many of the fundamental necessities for LIRIC. The new scanning modality allowed for faster speeds with smoother velocity profiles when compared to linear or piezo stages. In comparison with the first in vivo prototype, System 1, the flexure-based scanner increased the achievable pattern size to be clinically relevant, with a maximum stroke of over 8 mm. The addition of an AOM for active intensity control enabled the system to create spatially varying GRIN patterns with high precision and speed. For the first time, a variable dispersion compensator subsystem was implemented. That, along with the variable effective NA of the system, play a role in exploring the full parameter space of LIRIC.

While System 2 met most of the design considerations for a successful LIRIC system, the flexure design caused failure of the scanner over continued use. Therefore, a new, more mechanically robust scanning modality was developed.

System 3: Galvanometer Scanning System

System 3, the next iteration of LIRIC, implements a 2D galvanometer scanning system which exploits the field of view of the microscope objective as well as stitching techniques to create large area GRIN patterns. In the initial stages of LIRIC design, the sample was translated beneath stationary objects. In the second iteration, the microscope objective was translated above a stationary sample, facilitating in vivo studies. In System 3, all optics remain largely stationary. Instead, the focal spot is translated by utilizing the field of view of a stationary microscope objective to inscribe GRIN lines over small areas. Then, stitching techniques are employed to construct large area patterns.

Figure 14:
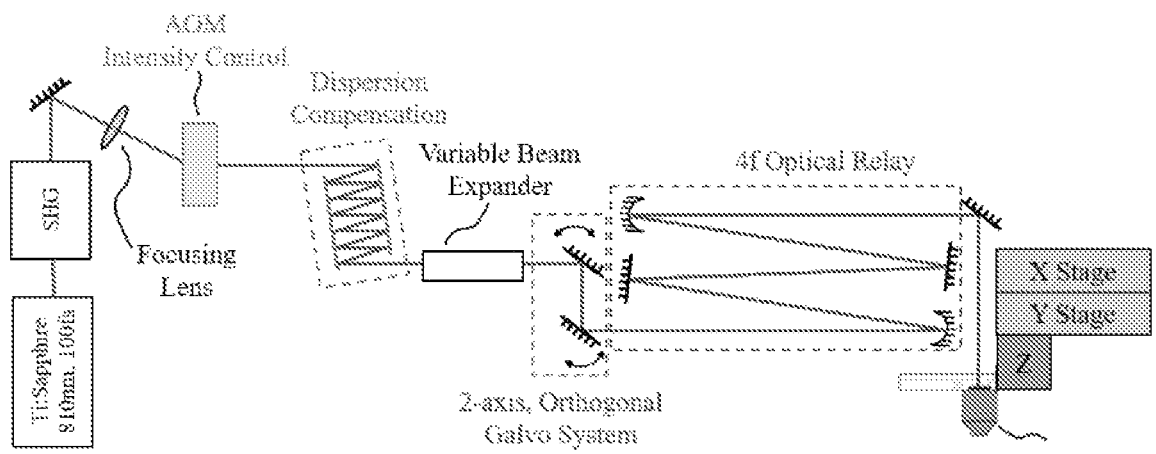
FIG. 14: Schematic of System 3. A Ti:Sapphire oscillator produced 810 nm, 100 fs pulses which were frequency doubled to 405 nm. An AOM was used to modulate the intensity of the laser in real time. Then, the beam bounced between two GTI mirrors for pulse compression. A variable beam expander controlled the NA and a 4f relay was used to route the beam into the final scanning system. A two axis, orthogonal galvanometer system, in conjunction with linear stages, was used to raster scan the focal region within a sample to create 3D LIRIC structures.
Figure 15:
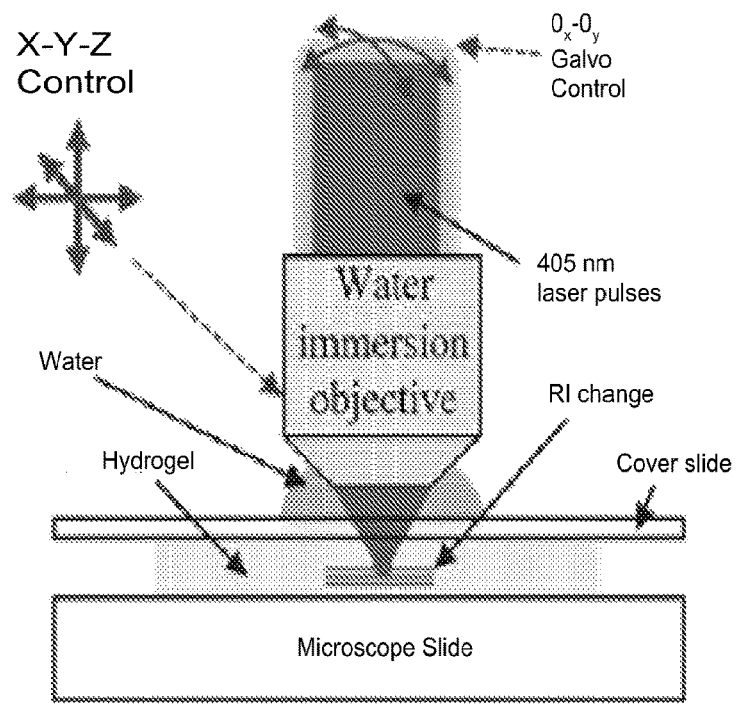
FIG. 15: Schematic of the LIRIC writing in hydrogels using System 3. The 2D galvanometer controls the angle of incidence of the laser beam, scanning the focal volume through the FOV of the microscope objective in one direction. A linear stage translates the microscope objective in the orthogonal direction, creating a raster scan pattern.

The optical elements of System 3 are largely the same as System 2. The system incorporates an AOM for active intensity control, contained a dispersion compensation subsystem, and utilized a variable beam expander to control NA (FIG. 14). In contrast, System 3 scanning system combined a two-dimensional orthogonal mirror galvanometer with three linear stages to create 3D LIRIC structures. This allowed for more precise control of both the position and velocity of the focal volume. This system was designed and built by Clerio Vision Inc., under a research contract with the University of Rochester. The combination of linear stages and a 2-axis orthogonal galvanometer scanning system (AGV-14HPO-RSE-ES18575; Aerotech, Inc.) allowed for high speed writing of small area structures that were then stitched together. The 2-axis galvanometer changed the angle of incidence of the laser beam on the microscope objective, scanning the focal volume through the field of view (FOV), as shown in FIG. 15.

Figure 16:
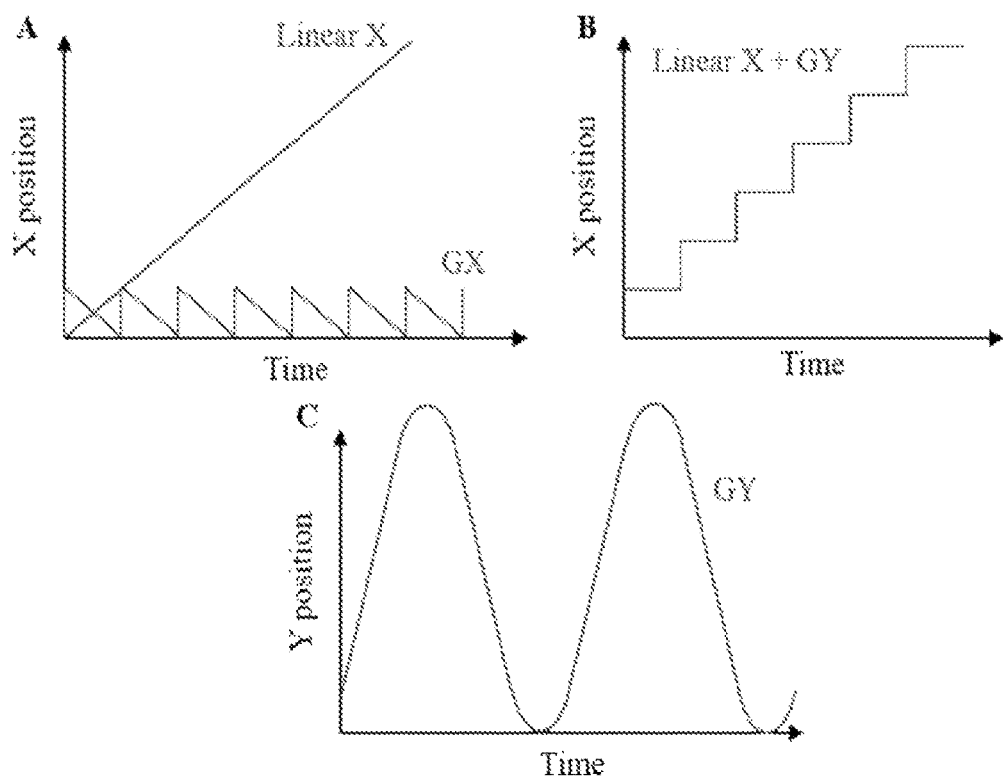
FIG. 16: Schematic of linear X, GX, and GY stage motions. The linear X stage translates the objective as the GY scans the focal volume through the FOV of the microscope, and the GX stage creates step overs during the GY turn around points. The GY velocity profile is constant except during the turnarounds. This combined motion creates a raster scan pattern with a uniform line spacing.

As the Y-axis of the galvanometer (GY) was scanning the focal volume through the FOV, a linear X-stage (ANT130-060-L-25DU-NONE; Acrotech Corporation) was slowly translating the objective. Simultaneously, the X-axis of the galvanometer (GX) was compensating for this motion. The GY velocity profile was linear except in the turnaround areas at the limit of the FOV. During the turnarounds, as with System 2, the AOM was synchronized with the stages and blocked laser power to the $1^{st}$ order diffracted beam in order to avoid damage during the zero velocity moments. The motion profiles of all the relevant stages are shown in FIG. 16. The combination of galvanometer motion and linear stages created a raster scan pattern with uniform line spacing.

Once a raster scan pattern had been complete (i.e. had reached the necessary length in the X direction), the linear Y stage (ANT130-060-L-25DU-NONE; Aerotech Corporation) would move the objective to an adjacent region where the raster scan process began again. Precise control of the linear Y stage ensured there was no overlap or space between the two adjacent written areas. Through this technique of stitching, large area patterns could be written. In System 3, the length of a single GRIN line (from the GY scan) was limited to 1 mm. While the FOV of the microscope objective (XLPLN25XWMP2; Olympus Corporation), was larger than 1 mm, there was a field dependence at the edges of the FOV. The light would experience higher order aberrations at the far edges of the field, and a significant decrease in induced phase was seen. If the GY scan was limited 1 mm scan, the phase change was uniform. An example of a LIRIC lenticular structure with stitching zones is shown in FIG. 17B. The edges of the stitching zones were apparent in DIC microscopy (FIG. 17A).

The laser source used in System 3 is a Ti:Sapphire oscillator (Mai Tai HP, Spectra-Physics Corporation). The laser generated up to 3 W of 810 nm, 100 fs pulses at an 80 MHz repetition rate. The light was frequency doubled to 405 nm through second harmonic generation. The laser intensity control for System 3 was identical to that of System 2. In short, the light was focused into an AOM (M113-aQ80L-2; Isomet Corp.) using a 500 mm focal length lens. The first order beam was picked off, and the intensity was modulated via a voltage signal to the AOM driver with MHz bandwidth.

Like System 2, System 3 incorporated dispersion compensation to minimize pulse width in the focal region. However, instead of a double pass prism configuration, System 3 utilized Gires-Tournois interferometer (GTI) type negative dispersion mirrors. GTI mirrors are optical standing wave resonators, or etalons, designed to generate chromatic dispersion. This chromatic dispersion is used to compress pulsed light. In design, the front side of the mirror is partially reflective, and the back side has high reflectivity, approaching 100%. When a plane wave is incident on a GTI at angle θ, as shown in FIG. 18 the reflected plan wave can be represented by $$\Psi e^{i\omega x} = \frac{-r + e^{i\omega\Delta\varphi}}{1 - re^{i\omega\Delta\varphi}} e^{i\omega x} \text{ and } \Delta\varphi = \frac{2dn\cos\theta}{c}, \quad (2.18)$$

where Ψ is the complex amplitude, ω is the angular frequency of the wave, r is the reflection coefficient (if r is real, the r is equal to the square root of the reflectance), d is the thickness of the mirror, n is the index of refraction of the mirror, θ is the angle of incidence, and c is the speed of light.

If the angle of incidence is fixed, then r is periodic with respect to wavelength. To control the phase change, and thereby the group delay, the reflectance of the front mirror is changed. By using two parallel mirrors and bouncing between them, the group delay can be increased, and the pulse compressed. For System 3, the light was bounced six times per mirror to produce a minimum pulse width of ~165 fs in the focal plane.

Similarly to the flexure-based system, System 3 employed a Galilean beam expander (FIG. 11) with several lens combinations in order to study the effect of various NA in hydrogel and cornea. The lenses and their resulting NAs are listed in Table 3. Unlike System 2, this system did not experience a power-dependent NA, most likely due to the implementation of GTI mirrors instead of prisms in the pulse compression subsystem, which eliminated possible thermal lensing issues. All NAs were measured using the knife edge test may times over the course of a few weeks to ensure repeatability. One final difference between Systems 2 and 3 was that some of the beams exiting the beam expander in System 3 were diverging slightly. After the AOM, the beam was not recollimated as the small divergence was deemed acceptable for the system.

TABLE 3

The focal lengths and effective NAs for the for beam expander configurations in System 3.

| F1 [mm] | F2 [mm] | Effective NA | Beam State |
|---|---|---|---|
| −100 | +200 | 0.19 | Collimated |
| −100 | +150 | 0.26 | Collimated |
| −100 | +150 | 0.32 | Diverging |
| — | — | 0.49 | Diverging |

After passing through the beam expander, the light was directed into a reflective 4f relay before being sent into the 3 axis beam delivery system. This system ensured the beam was aligned to all three mechanical axes of motion to prevent beam walk. Finally, the light was directed into the NA 1.05 water immersion objective, whereupon it was focused into a sample to generate LIRIC structures in hydrogel or corneal tissue. By combining high speed galvanometer with large area linear stages, System 3 is capable of creating large area LIRIC patterns quickly and precisely. AOM intensity control allows precise modulation of the induced RI in real time. Additionally, the dispersion compensation subsystem has eliminated thermal lensing issues seen with the prisms in System 2. Overall, System 3 provides an improvement towards a high-throughput contact lens manufacturing system as well as a non-invasive alternative for vision correction.

Mach-Zehnder Interferometer

Figure 19:
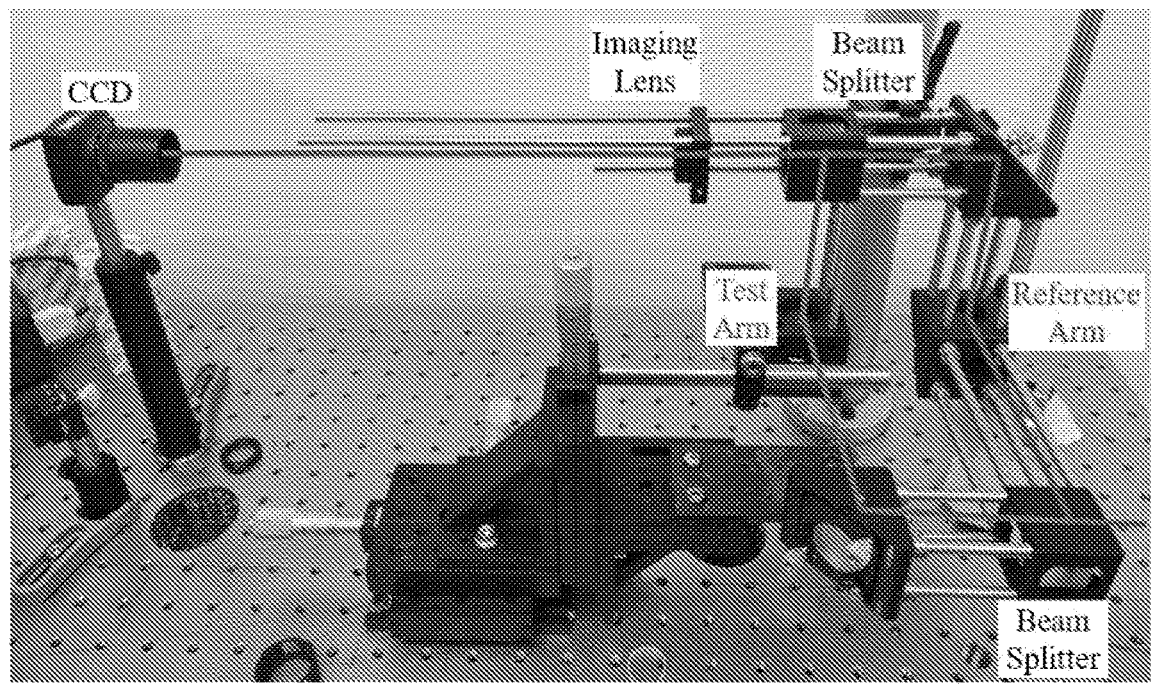
FIG. 19: Beam path through the Mach-Zehnder Interferometer. The laser light from the source (HeNe operating at 632.8 nm) is split into the test (blue) and reference (red) arms. After being recombined, the light is imaged onto a CCD where the fringes are recorded. The phase difference between the two arms is later calculated.

There are two ways to quantify the effect of LIRIC: refractive index change and phase change. While the two are proportionally linked by Equation (2.1), induced phase change is of greater importance when considering how to design refractive correctors. For lenticular structures such as Fresnel lenses, the bulk phase change is of greater importance. Therefore, a means of measuring bulk phase change is required. To do so, a Mach-Zehnder Interferometer (MZI) was built to test LIRIC samples. A MZI is a single-pass, open path interferometer. A MZI measures samples in transmission, which is relevant to vision correction optics. Light is split into two paths, a test arm which passes through the test optic or sample, and a reference arm where the light is unaltered. The light is then recombined. The dark and light fringes that results from this interference are then recorded on a CCD camera in order to collect the phase information over the CCD's FOV. It is important that the sample plane be conjugate to the detector plane to accurately capture the phase difference between the two arms of the interferometer. A photograph of the MZI used is shown in FIG. 19.

To measure the induced phase change of LIRIC, rectangles of constant phase were inscribed into samples. The size and shape of these bars was dependent on the FOV of the CCD used to measure them. These groups of phase bars will be referred to as phase carpets. In general, areas of constant phase were inscribed in samples and then that bulk phase was compared to that of the native background. The induced phase change is simply the difference between the LIRIC-treated area and the unaltered material surrounding the phase bar.

Once an image of a phase bar was captured, a Fourier Transform-based algorithm was used to extract the induced optical phase change. Carrier fringes were added to the CCD images by inducing tilt between the test and reference wavefronts by manually adjusting mirrors in either the test or reference arm. For the algorithm used, it was necessary to have horizontally or vertically aligned fringes. The frequency of the fringes must be adjusted such that it is resolvable by the imaging system.

Figure 20A:
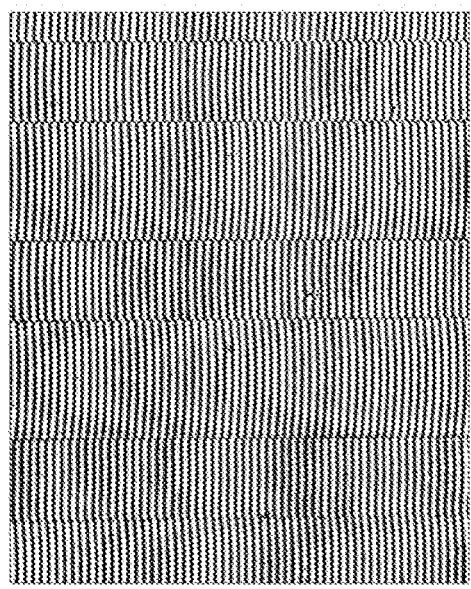
FIGS. 20A and 20B: Interferogram and resulting phase map of three bars of constant phase written with LIRIC.
Figure 20B:
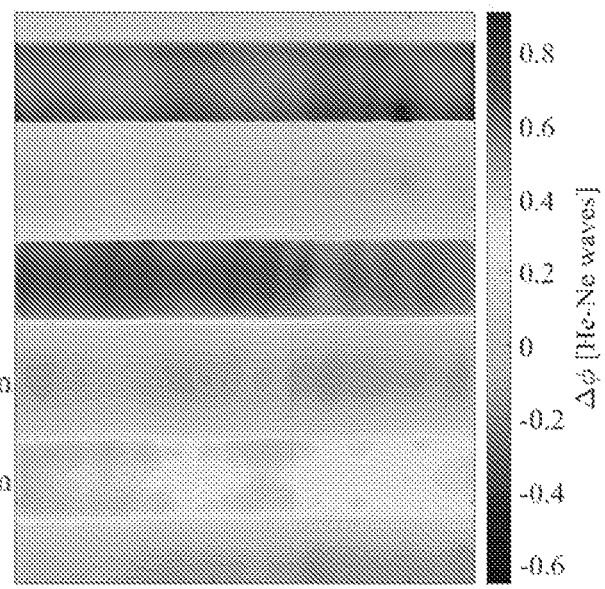

The interferograms collected by the CCD were read into a custom MATLAB program. A Fourier Transform was computed on the image to produce the frequency spectrum. This generated a large central peak and two smaller peaks around the origin. One of these high-frequency peaks is selected and shifted to the origin. The other two peaks are removed. The remaining frequency contained the desired phase was then inverse Fourier transformed to return to the spatial domain. Finally, phase unwrapping was performed using a Goldstein phase unwrapping algorithm. An example of an interferogram and its resulting phase map are shown in FIGS. 20A and 20B.

In a single interferogram, the sign of the phase change is ambiguous. A technique employing a single-axis phase ramp may be used to determine the sign of phase change in LIRIC bulk phase samples. It was determined that LIRIC induces a negative phase change in the hydrogel material Contamac 58, and that cornea experiences an increase in bulk phase following the LIRIC procedure.

Design of Experiments

LIRIC is a complex, multiphoton process that depends on many parameters, including laser power, laser pulse width, effective NA, line spacing, scan speed, and sample material composition. Because LIRIC is a complicated laser-material interaction, interdependencies between parameters define a narrow range of combinations that produce the desired effect. The aim of the following experiments was is to explore LIRIC parameter space and maximize the efficacy of the process in hydrogel material. This includes exploring the parameters' impacts on induced phase change and the damage threshold. The work was done on Systems 2 and 3 described above.

As a multiphoton process, the induced phase change is exposure-based. For example, if the peak intensity in the focal volume were higher, the dwell time of the laser could be decreased, and vice versa. The peak power of a pulse depends on the average power and the pulse width of the laser and is given by $$P_{peak} = \frac{P_{avg}}{\tau RR} \tag{3.1}$$

where Pavg is the average power of the laser, $\tau$ is the pulse width, and RR is the repetition rate. For the following described experiments, only the first two variables were adjustable.

Figure 21:
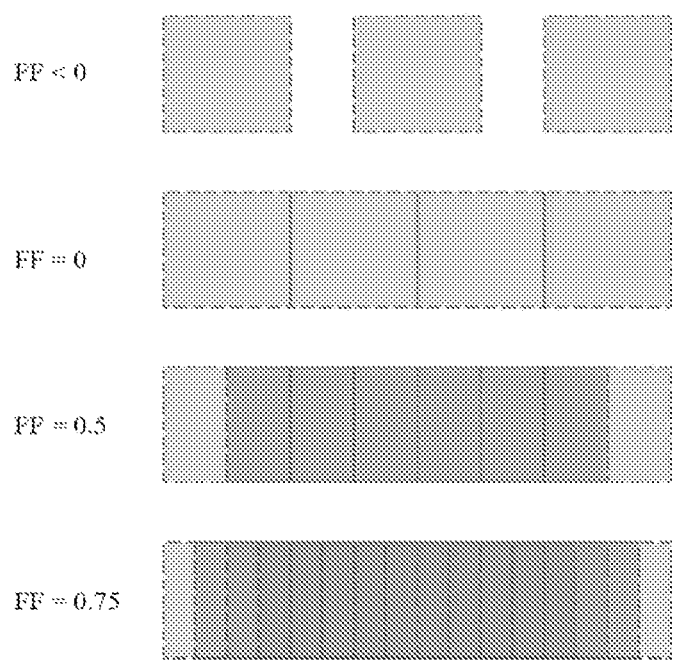
FIG. 21: Illustration of various fill factors. Fill factor represents the amount of overlap between adjacent LIRIC lines, with a fill factor of zero representing no overlap, and a fill factor of 0.5 indicating half of the adjacent line overlaps the previous line.

Another important parameter is the combination of interaction region and line spacing, termed "fill factor." Fill factor may be mathematically represented as $$FF = \frac{\omega - \Delta \ell}{\omega} \tag{3.2}$$

where FF is the fill factor, $\omega$ is the diameter of the beam in the focal plane, and $\Delta l$ is the line spacing. If the NA were to be reduced, thereby increasing the interaction volume of the laser, the line spacing could be correspondingly increased while maintaining an acceptable fill factor. Fill factor is defined as the percentage overlap of adjacent LIRIC lines. For example, if the focal spot diameter is 1 μm, and the line spacing is 0.5 μm, the fill factor is 0.5. If the line spacing is equal to the width of the GRIN line, then there is no overlap, but there will not be any unaltered space between them either, resulting in a fill factor of zero (FIG. 21).

The last adjustable variable for these experiments was the scan speed of the focal volume through the sample. In System 3, this is an easily controllable parameter. Previous studies have shown that, if all other parameters are the same, induced phase change is inversely proportional to scan speed. However, this previous work was done at scan speeds of less than 10 mm/s. Newer scanning modalities as described for Systems 1-3 allow for scans speeds over 200 mm/s. The scan speed couples with the repetition rate to determine the number of pulses per unit area. If the laser does not deliver enough pulses, then the RI change may not be sufficient. Other parameters, such as average power, pulse width, and fill factor can be used to compensate for higher speeds and maintain sufficient photo-modification. This complex parameter space was explored in an effort to determine an optimal combination of parameters.

Two proof-of-concept experiments were performed. In the first, the polarization state of the laser was changed to determine whether polarization affected the magnitude of induced phase change. Many materials are anisotropic and certain polarization states may be more easily absorbed. For this preliminary experiment, two orthogonal linear polarization states were used: parallel or perpendicular to the scanning direction. In the second experiment, it was noted that phase change in a LIRIC inscribed sample increased over time before plateauing, sometimes taking as long a month to stabilize. Phase change stability is of importance for the commercialization of LIRIC. Precise phase change is in particular of importance for the creation of Fresnel lenses, as if the inscribed phase change is not equal to 1 wave, the Fresnel lens will not be monofocal. In the same way, if the induced phase change is different from the prescribed value, a multifocal lens will have the incorrect diffraction efficiency. Therefore, to create a LIRIC nomogram, the exact phase change must be predictable and stable over time. Several methods for expediting the stabilization of phase change were investigated, and an approach to achieve long-term phase change stability was found.

Laser Systems 2 and 3 were used for the experiments. For both systems, a design of experiments (DOE) utilizing a full factorial design was devised. The two DOEs here explored the LIRIC parameter space and paved foundations for a hydrogel nomogram. These experiments helped provide a more in depth understanding of the interactions between the most fundamental LIRIC parameters and aided in stretching the dynamic range of LIRIC in hydrogels.

System 2, the flexure-based scanner, was used to study the effects of NA and pulse width on induced phase change and damage threshold. System 3, the galvo-linear system, was used to study the impact of fill factor and scan speed. In both cases, induced phase change was measured using the MZI as described above, and damage and phase change uniformity were assessed using differential interference contrast (DIC) microscopy (BX53; Olympus Corporation).

DOE 1: Flexure-Based System

Figure 22:
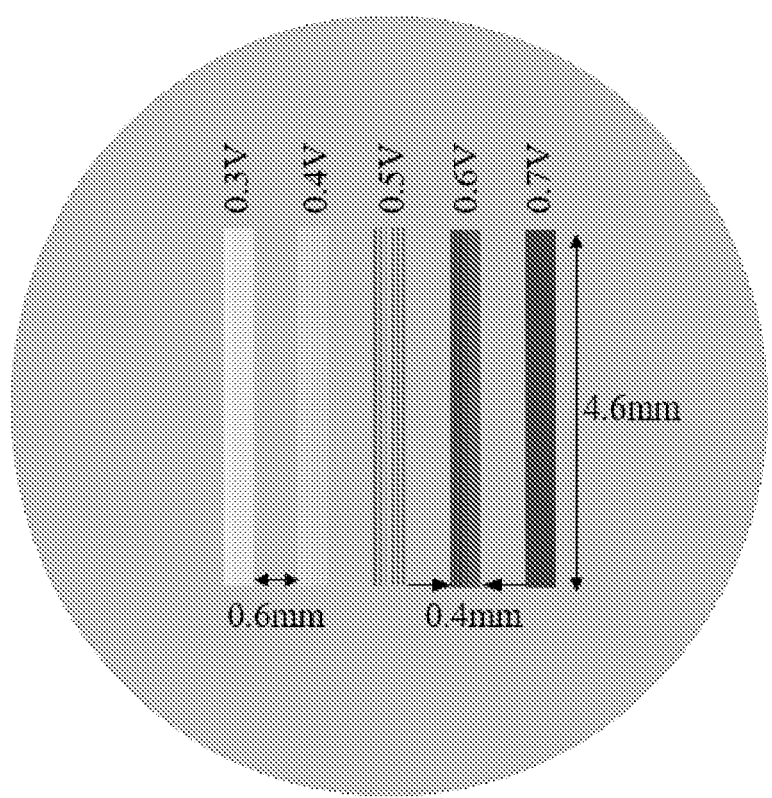
FIG. 22: Diagram of a phase carpet inscribed in Contamac 58 using System 2. Five bars of constant phase with dimensions of 4.6 mm by 0.4 mm were inscribed with different AOM voltages, producing bars of increasing bulk phase change.

For the first DOE, phase bars were created by using the flexure-based system. A hydrogel sample was sandwiched between a microscope slide and a #1 coverslip to reduce dehydration during the writing process. The laser's focal region was focused into the center of the sample, approximately 250 µm below the surface. The hydrogel material used was Contaflex GM Advance 58 (Contamac, Ltd.). This material will be referred to as Contamac 58. This material was chosen for its high water content, 58%, as well as its availability in flat buttons. Contamac 58 buttons are ~0.5 mm thick, allowing for multi-layer structures, like those used in in vivo experiments. Phase bars were written with a 0.5 µm line spacing and were 0.4 mm wide, with a spacing of 0.6 mm between adjacent bars (FIG. 22). The flexure oscillated with a 10 Hz frequency. For the twelve samples in the first DOE, the flexure had an average stroke of 4.6±0.2 mm and a scan speed of 145±5 mm/s. The FOV of the system was dictated by the size of the CCD used in the MZI (DCC1545M, Thor Labs) and the 1:1 magnification of the imaging system. The sensor (thus FOV) was approximately 3.3 mm by 2.7 mm, so the bulk phase was measured in the center of the phase bars, where the velocity profile was linear.

Figure 23:
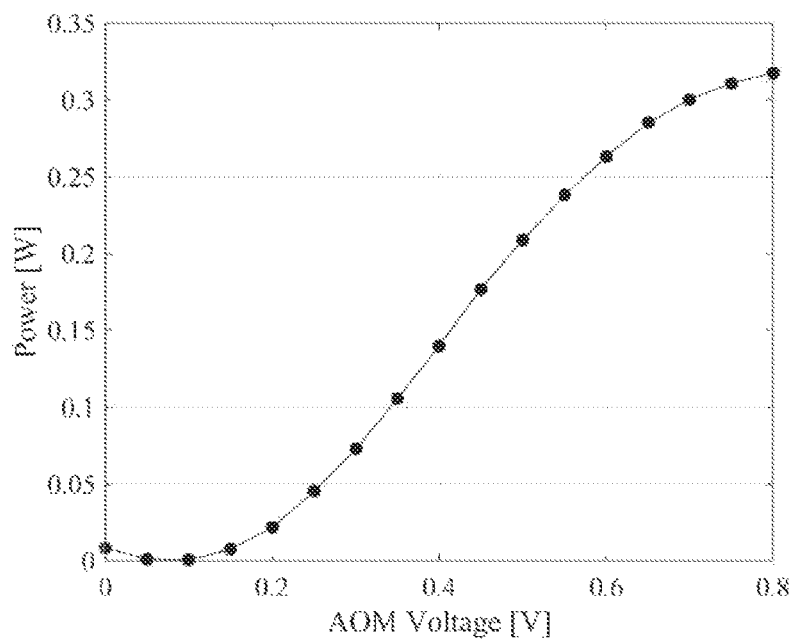
FIG. 23: AOM calibration taken before writing a phase carpet in Contamac 58 with System 2. The voltage signal to the AOM is slowly increased and the power is measured with a power meter directly after the microscope objective, with the detector in the focal plane.

In each sample, five different phase bars were inscribed, each with increasing power (FIG. 22). The AOM voltages were chosen to span a large average power range and increased from 0.3 V to 0.7 V in increments of 0.1 V. Before each sample was written, a power calibration curve was obtained. The voltage was increased incrementally from 0 V to 0.8 V in increments of 0.05 V. The power was recorded by a power meter placed immediately after the microscope objective to measure the average power in the focal plane. Due to mild fluctuations in the system, mostly stemming from small misalignments in the SHG, the average power for a given AOM voltage could fluctuate several milliwatts from day to day. AOM calibrations were recorded before every sample, allowing precise knowledge of the power applied to each phase bar. A sample power calibration curve is shown in FIG. 23.

Twelve samples were inscribed with phase carpets as described above and analyzed using the MZI. Each sample had a different beam expander ratio and pulse width combination. The twelve samples were created using a full factorial design with three beam expander ratios and four pulse widths. Due to thermal bloom in the prisms, the effective NA of the System 2 was power dependent, with NA varying up to 0.15 over the power range used in the phase carpets. The pulse widths were determined by the 45° mirrors' positions on the carriage rails used to adjust the prism separation distance in the pulse compression subsystem. Each pulse width was individually measured for each sample. The pulse widths were ~165, 180, 210, or 350 fs.

DOE 2: Galvanometer-Based System

As with the previous DOE, this experiment used a full factorial design. However, a different set of parameters was the focus. Given the configuration of the GTI mirrors used for dispersion compensation, a variable pulse width was not obtainable in System 3, and dispersion was left at a minimum value of ~165 fs for this experiment. Instead of pulse width, fill factor and scan speed were the dependent variables for this experiment. To control fill factor, four different beam expanders were used in conjunction with three different line spacings. The effective NAs for the study were 0.19, 0.26, 0.30, or 0.49. The corresponding diffraction limited spot size for each NA is given by $$D = \frac{1.22\lambda}{NA} \tag{3.3}$$

where D is the diameter of the spot in the focal plane, and λ is the wavelength of light.

The line spacings studied were 0.3, 0.5, and 0.7 µm. Therefore, using Equations (3.2) and (3.3), it was calculated that the fill factors for this DOE ranged from 0.31 to 0.81. For each NA, 9 phase carpets were written, generating a total of 36 phase carpets that were analyzed for DOE 2.

Figures 24A, 24B:
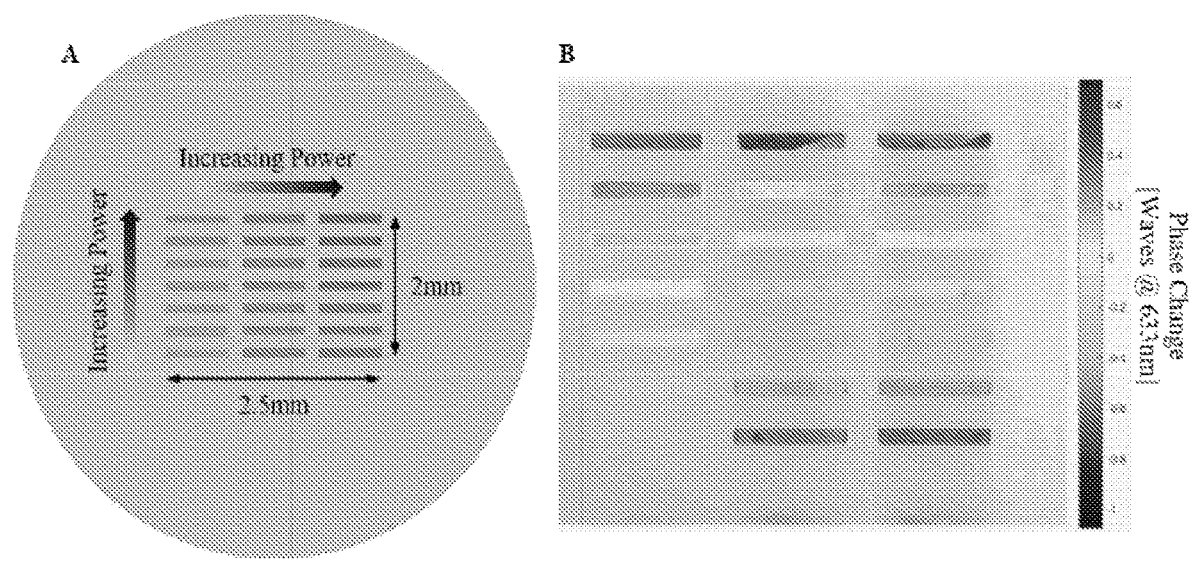
FIG. 24A: Diagram of a phase carpet inscribed in Contamac 58 using System 3. Twenty-one bars of constant phase with dimensions of 0.72 mm by 0.1 mm were inscribed with different AOM voltages, producing bars of increasing bulk phase change. Figure not to scale.
FIG. 24B: Resulting phase map of a System 3 phase carpet.

Phase carpets were inscribed into the middle of Contamac 58 hydrogel samples, approximately 250 µm below the surface. Each phase carpet consisted of 21 bars of constant phase. Speed and line spacing remained the same while power was increased from 15 mW to 275 mW in equal increments. As with System 2, an AOM power calibration was performed before every test to ensure all phase bars received the correct laser power dosage. A diagram of a System 3 phase carpet is shown in FIG. 24A. Phase bars were 0.72 mm in length to ensure phase change uniformity, as field dependence in the microscope objective could lead to reduced phase change near the edge of the field in the GY scan. The phase bars were 0.1 mm in height and were separated by 0.2 mm in both the X and Y directions.

The phase carpets for System 3 were designed such that all 21 phase bars fit within the MZI's FOV, with the total phase carpet occupying a 2.5 mm by 2 mm area. Then, using a custom MATLAB program, all 21 bars were analyzed simultaneously. Fourier Transform and phase unwrapping techniques were used to extract the phase (FIG. 24B).

Polarization Dependence Experiment

In System 3, the nominal polarization of the laser entering the microscope is horizontally polarized with respect to the optical bench. This polarization state is also parallel to the LIRIC scanning direction. To achieve the orthogonal polarization state, a half-wave ($\lambda/2$) plate (HWP) designed for 405 nm (WPHSM05-405, Thor Labs) was placed in the optical beam path before the beam expander with the fast axis at 45°. A wave plate is an optical retarder, and a HWP produces a $\lambda/2$ phase shift for a particular design wavelength. A HWP can rotate linearly polarized light by twice the angle between the fast axis and the plane of polarization. Therefore, in System 3, the incident horizontally polarized light will exit the HWP vertically polarized. Vertically polarized light will have the plane of polarization perpendicular to the scan direction of System 3.

Phase carpets were written with orthogonal polarization in the same hydrogel sample. The other salient LIRIC parameters are shown in Table 4. The phase carpets were then imaged in the MZI and analyzed as described previously. The magnitude of phase change as well as the shape of the phase change versus laser power curves were directly compared.

TABLE 4

LIRIC writing parameters for phase carpets with horizontal or vertical polarization

| Parameter | Value |
| --- | --- |
| Effective NA | 0.19 |
| Scan Speed | 200 mm/s |
| Line Spacing | 0.5 µm |
| Power | 10-210 mWs |
| Pulse Width | 165 fs |
| Depth | 250 µm |
| Material | Contamac 58 |

Long-Term Phase Change Stability

The 36 phase carpets created for DOE 2 were monitored over time for a period of up to one year. During this time, the Contamac 58 samples containing the phase carpets were stored in the saline solution in which they originally arrived. The induced phase change was measured in the MZI and analyzed as described previously.

A further set of 8 new phase carpets was also created to investigate methods for stabilizing the induced phase change. All phase carpets were written using System 3 with an effective NA of 0.19, a scan speed of 200 mm/s, and a line spacing of 0.5 µm. Several phase carpets were kept as controls for comparison. All samples were measured and analyzed in the MZI at the following time points post-LIRIC: 1 hour, 7, 14, 28, and 88 days.

Six of the phase carpets were used to test the effects of different storage media and sterilization processes. Any commercial contact lenses created with LIRIC would be sterilized with an autoclave; therefore, the effect of the process on induced phase change was studied. Three samples in their original saline solution were processed with an autoclave at 121° C. at 15.3 psi for 30 minutes. An autoclave is a heated, pressurized chamber used for industrial sterilization. Interferograms were taken immediately before and an hour after being processed in the autoclave. The remaining three samples were stored in distilled water, n-Propyl alcohol, or a commercially available contact lens solution (PuriLens, Life Style Inc.) 35 days after the phase carpets were written. For these experiments, interferograms were taken immediately before being placed in the new fluid and after soaking for one hour. The samples were measured again after 7, 14, 28, and 88 days to see if and/or when the test condition resulted in a stabilization of induced phase change.

Results

DOE 1: Longer Pulse Widths Increased Laser Damage Threshold

Figure 25:
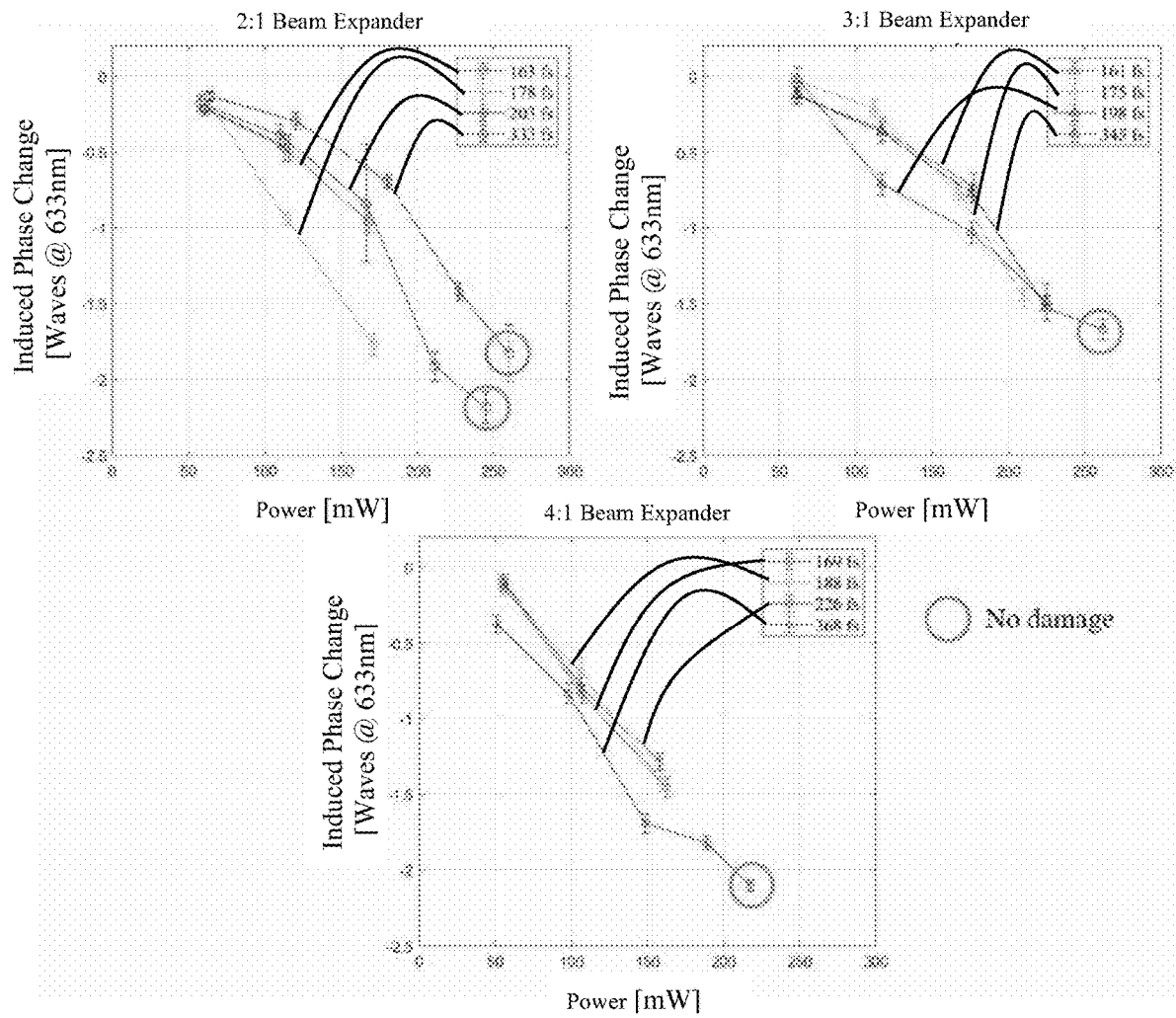
FIG. 25: The results from the 12 phase carpets written using a full factorial design DOE on the flexure system. The phase change induced by unique combinations of three different beam expanders and four different pulse widths were measured. No damage was seen at the longest pulse width for all beam expanders (large circles) and the second longest pulse width for the 2:1 configuration.

The results from the flexure system DOE are shown in FIG. 25. The maximum phase change, −2.2 waves at 633 nm, was achieved using the 2:1 beam expander with a pulse width of 203 fs. In general, the phase change exhibited in the 4:1 beam expander phase carpets was lower than the other two configurations. However, at the longest pulse width of 368 fs, the 4:1 beam expander produced the second highest phase change, with a magnitude of 2.1 waves at 633 nm. Of the 12 phase carpets, only four did not experience laser damage at the highest laser power, ~250 mW: all three of the longest pulse widths and the 2nd longest pulse width in the 2:1 configuration. These phase carpets are denoted by large circles in FIG. 25.

Figure 26:
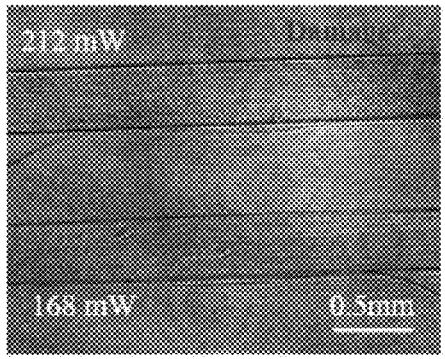
FIG. 26: Bright field image taken with the MZI CCD of two phase bars. The top bar exhibits laser damage at 212 mW. Note dimpling or pockmarks in top bar.

Due to the limited aims of this preliminary study and large power steps in the phase carpets, bright field images in the MZI were deemed sufficient to classify laser damage. An example of laser damage seen in bright field is shown in FIG. 26.

Figure 27:
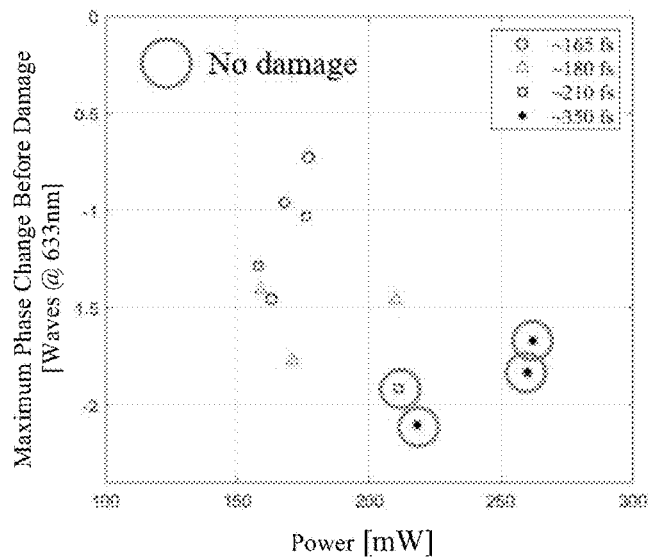
FIG. 27: Maximum phase change before damage for all 12 phase carpets written on the flexure system. The highest magnitudes of phase change corresponded with the longest pulse widths. The three maximum pulse widths were undamaged, as was the lowest NA's 2nd longest pulse width (large circles).

None of the trials involving the longest pulse width produced damage. FIG. 27 shows the maximum phase change before damage for all 12 phase carpets, with the four undamaged phase bars circled. It was clear from those data that long pulse widths allowed more laser energy to be deposited in the sample before laser damage occurred. Accordingly, the maximum phase change achieved was correlated with pulse width. Additionally, no damage occurred in the second longest pulse width at the lowest NA. All four undamaged trials had the lowest peak energy densities.

DOE 2: Combinations of Fill Factor and Scan Speed Increased LIRIC Dynamic Range

Figure 28:
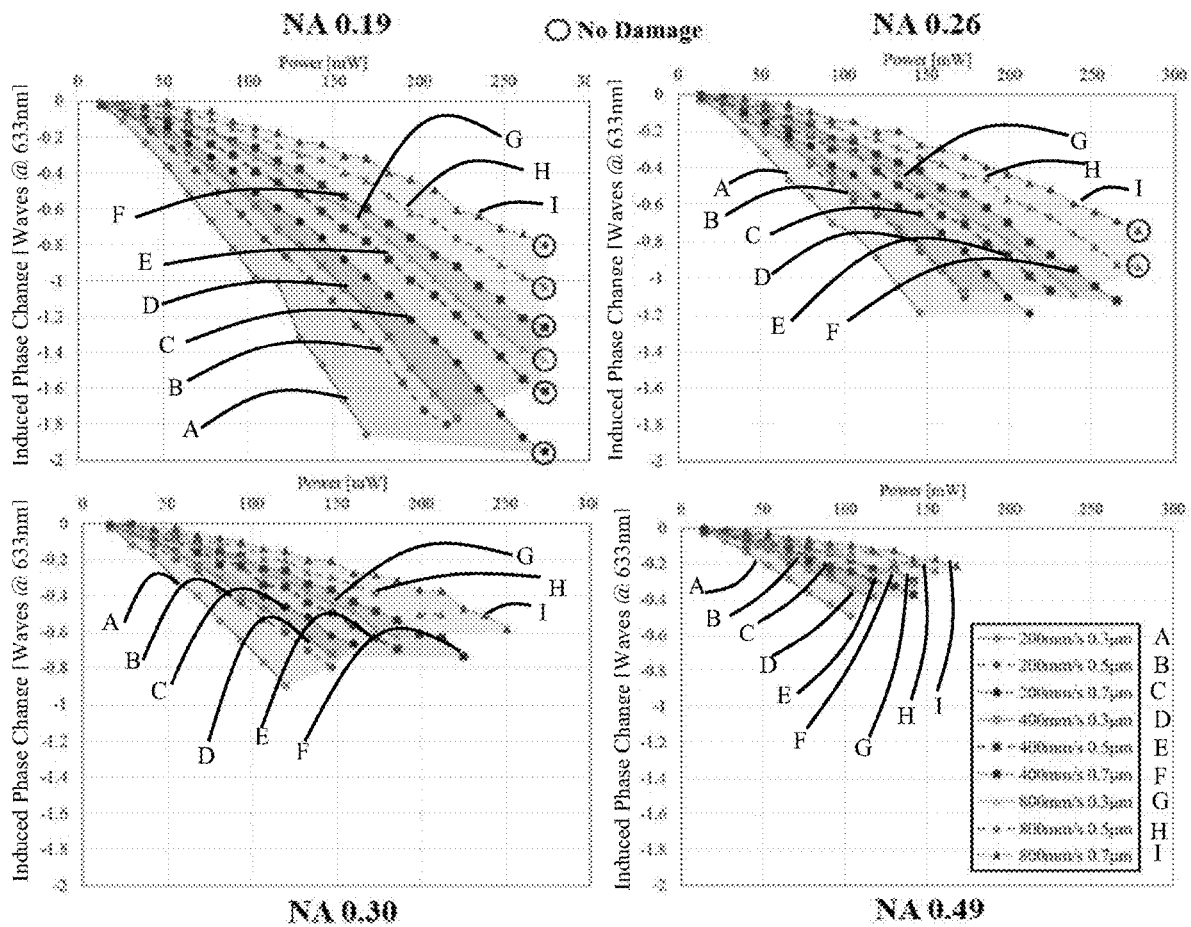
FIG. 28: Results from System 3's DOE. Shaded areas represent the dynamic range of each speed per a particular effective NA. The overall dynamic range of LIRIC increased as effective NA decreased. The maximum phase change achievable also significantly increased with smaller NAs. Circles mark phase carpets whose maximum power phase bar did not experience laser damage. High phase change was achievable at lower laser powers for slower speeds and tighter line spacing. Legend is the same for all graphs.

Thirty six phase carpets, each with a unique combination of effective NA, scan speed, and line spacing were analyzed. The results are shown in FIG. 28. The shaded regions represent the dynamic range of possible phase change achievable with each scan speed.

The maximum magnitude of induced phase change increased as the effective NA decreased, as did the overall dynamic range. A larger dynamic range is desirable as it allows for more precise control of LIRIC induced phase change. A larger operational parameter space allows the most precise parameters to be chosen for a specific application. Furthermore, out of the 36 phase carpets, only eight phase carpets did not experience laser damage at the maximum power, 275 mW. Six of those phase carpets were at NA=0.19, and two were the high speed, NA=0.26 carpets (circled in FIG. 28). The slope of the phase change curves represents the amount of phase change achievable for a given laser power, with steeper slopes representing more efficient LIRIC. The slope of the curves were also inversely proportional to the effective NA. Slower speeds and tighter line spacing also allowed for high phase change at lower laser powers.

Figure 29:
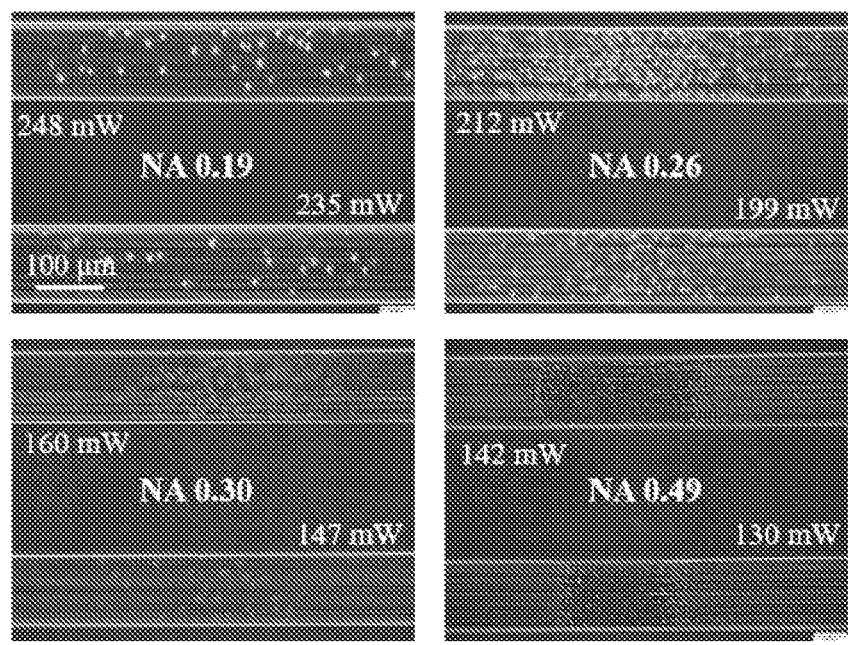
FIG. 29: DIC micrographs of laser damage in four different phase carpets from System 3's DOE. All phase carpets were written at 200 mm/s with 0.5 μm line spacing. The micrographs show the first two phase bars containing damage for each effective NA. Laser damage at the highest NA appeared as carbonization in the central region of the phase bar, while at lower NAs it appeared as discrete points across the whole phase bar. Scale is the same for all micrographs.

Laser damage was assessed using DIC microscopy. Examples of damage at different effective NAs are shown in FIG. 29. Damage occurred at higher laser powers in lower NA writing. Furthermore, the appearance of the damage differed between the high and low NA writing. In the NA=0.49 phase carpets, damage appeared as carbonization in the center of the phase bar and progressively grew to cover the whole phase bar as power increased. In the low NA writing, damage appeared as small, discrete damage areas.

Figure 30:
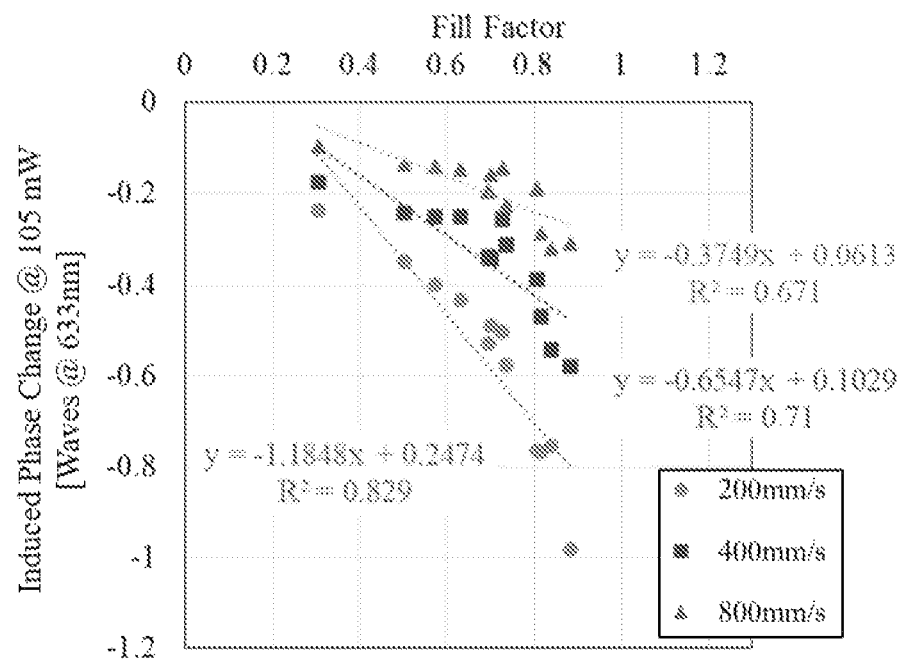
FIG. 30: Induced phase change at 105 mW for all 36 phase carpets in DOE as a function of fill factor. A linear regression fit showed fill factor had a significant effect on induced phase change.

In order to get the most meaning from the 36 samples written with different beam expanders, the effective NAs and line spacings were combined to examine the effects of fill factor. As described previously, fill factor is the percentage overlap between adjacent LIRIC lines (Equation (3.2)). By examining the dynamic ranges for each scan speed (shaded regions in FIG. 28), it was clear that both line spacing and NA greatly influenced the achievable phase change. Therefore, phase change at a given laser power, 105 mW was compared for all 36 phase carpets in order to determine the dependence on fill factor (FIG. 30). No phase carpet experienced laser damage at this power.

For a given laser power below the damage threshold for a set of LIRIC parameters, the induced phase change was proportional to fill factor. The data shown in FIG. 30 revealed a correlation between fill factor and induced phase change.

Figure 31:
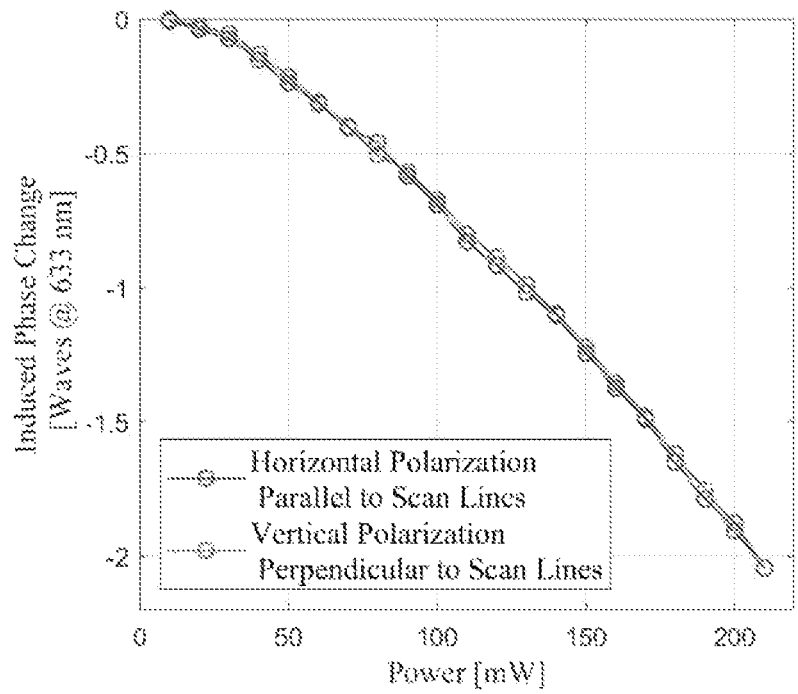
FIG. 31: Measured phase change from two phase carpets written using System 3 in Contamac 58 with either horizontal (blue) or vertical (red) polarization. Horizontal polarization is the native polarization state of System 3. The two orthogonal polarization states had nearly identical induced phase change at all laser powers.

Linear Polarization States Had No Effect on the Magnitude of Induced Phase Change The induced phase change achieved with either vertical or horizontal polarization is shown in FIG. 31. Phase carpets were written in the same hydrogel sample with the same AOM calibration and were analyzed one hour after writing. There is no significant difference between the two phase carpets at any laser power. The plane of polarization relative to the scanning direction was found not to influence the magnitude of induced phase change.

Long-Term Phase Change Stability

An initial investigation into long-term phase change stability in LIRIC-treated hydrogels revealed that phase change continued to increase over time, for up to a year. All samples from DOE 2 were tracked over time. All samples displayed approximately the same percent increase in phase change over time. In 11 to 15 days, phase change increased by ~9% for all samples. Over the first month, a 15% increase in induced phase change was seen. Since the two DOEs revealed that NA-0.19 was most efficacious for Contamac 58, the phase carpets written on System 3 with that NA were tracked the longest. After 100 days, the maximum phase change before damage in all nine phase carpets had increased 21±4%.

Figure 32:
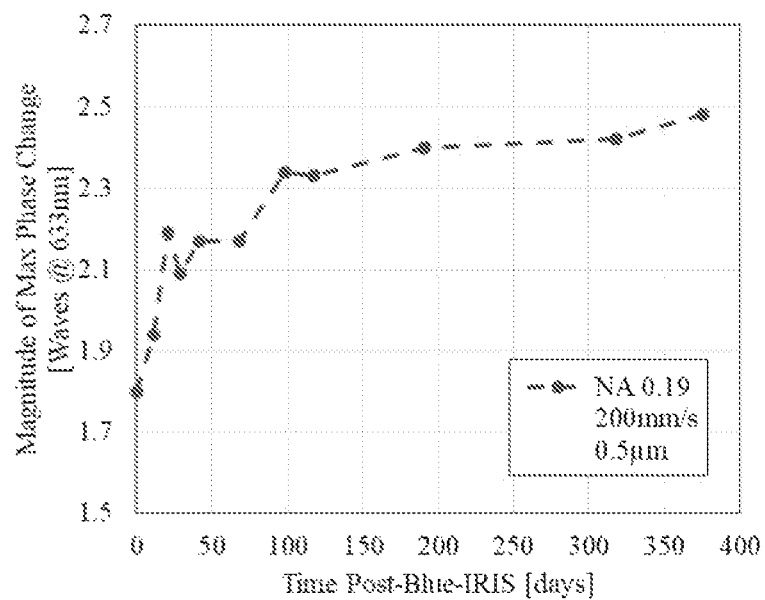
FIG. 32: Magnitude of time dependent phase change seen in a Contamac 58 sample with writing parameters: NA=0.19, 200 mm/s scan speed, and 0.5 μm line spacing. Average laser power in the focal volume was 216 mW. The sample was measured 11 times over the course of one year.

FIG. 32 shows the time dependent phase change of one sample, tracked for one year. Phase change was measured in the MZI as previously described. The phase carpet in the example below was inscribed on System 3 using an effective NA of 0.19, 200 mm/s scan speed, 0.5 μm line spacing, and an average laser power of 216 mW. All other samples from DOE 2 were tracked over time, many up to 300 days. All samples followed a similar pattern.

While the increase in phase change slowed over time, the phase change was not entirely stable until ~180 days. Minor fluctuations in the MZI resulted in a noise floor of ~0.1 wave at 633 nm. Therefore, some fluctuations in phase change over time were expected. Stability was defined as the point where the changes in phase change averaged to be zero over the course of a week. As with the other samples monitored over a long time, the majority of the increase in phase change occurred during the first month.

Figure 33:
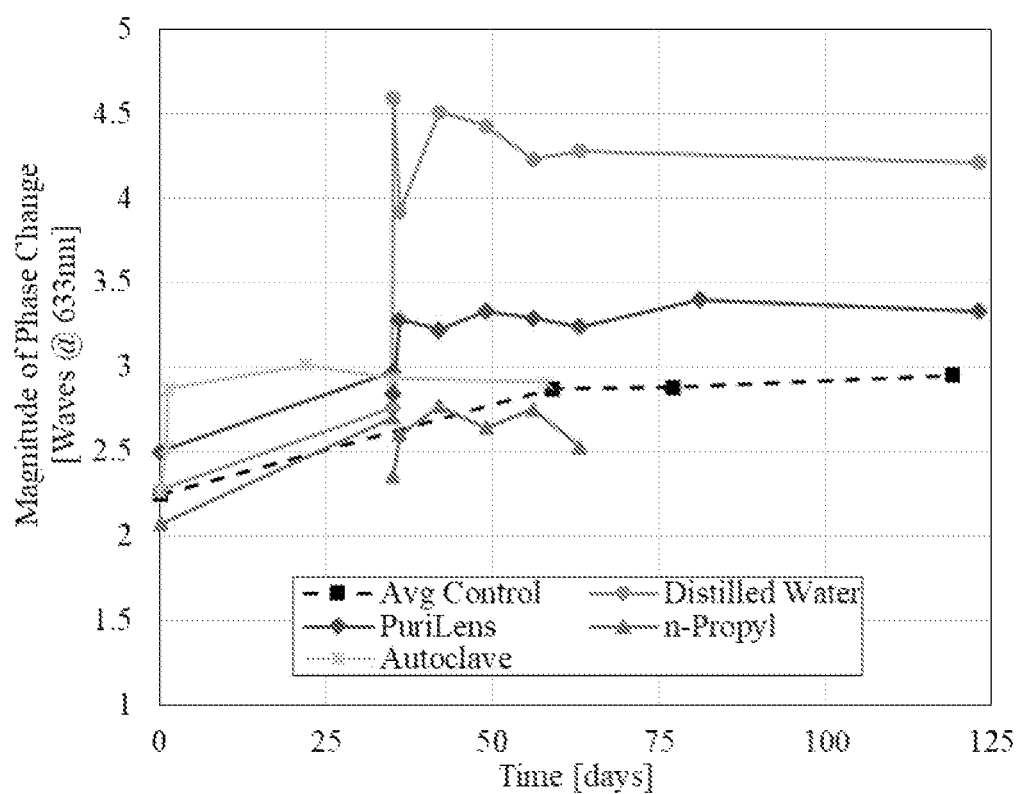
FIG. 33: Five Contamac 58 samples with LIRIC phase carpets were monitored over time. Three samples were placed in alternative storage media 36 days after LIRIC. Storage media were distilled water, PuriLens commercial contact lens solution, and n-Propyl alcohol. A fourth sample was processed in an autoclave one day after LIRIC. A control sample was also monitored.

The first three experiments into long-term stability of LIRIC phase carpets involved storing Contamac 58 samples in different storage media in an effort to expedite the diffusion process, which was hypothesized to be the cause of the time dependent increase in the magnitude of phase change. The results for three different storage media are shown in FIG. 33. The fourth experiment to halt the increase in phase change involved processing the sample in an autoclave. Three samples were created for testing in the autoclave process. However, two of the samples were not sent for processing until 35 days after LIRIC writing. Both samples suffered physical tears either during the process, or afterward during remounting of the sample for MZI measurement. In both cases, the data collected were unusable as the rips either penetrated the phase carpets or were directly adjacent to them, causing significant distortion of the carrier fringes in the interferograms. The third sample was autoclaved the day after LIRIC writing. No tears were seen and the interferograms were clear. The results from that sample are also shown FIG. 33.

The sample stored in distilled water experienced the most dramatic increase in phase change. After one hour in distilled water, the sample measured a 66% increase in the magnitude of induced phase. The maximum phase change reached −4.6 waves at 633 nm. The phase change dropped slightly the next day but stabilized to −4.3 waves at 633 nm within a week. The sample stored in PuriLens also experienced an immediate increase in phase, but stabilized immediately as well. The final magnitude of induced phase was ~17% greater than the pre-soak measurement. In both the distilled water and PuriLens samples, the final, stabilized phase change was significantly greater than the control sample's. All three samples were monitored to 123 days. The control sample appeared to stabilize around two months post-LIRIC.

The sample placed in n-Propyl alcohol did not experience an increase in phase change. In fact, when the sample was measured after one hour submersion in n-Propyl alcohol, the phase carpet was not visible in the MZI. The sample was returned to its original saline solution and re-measured after one hour. The phase carpet had reappeared, but the magnitude of phase change was unaffected.

Finally, the sample that was processed in the autoclave also underwent a rapid increase in the magnitude of induced phase change. The phase change increased by 27% compared to the pre-autoclave measurement. The induced phase change was immediately stable and remained so for the next two months at which point the final magnitude of phase change was approximately the same as the control sample.

The first DOE was devised in an attempt to find the extent of the NA and pulse width parameter space for LIRIC. This small full factorial DOE showed, for the first time, that minimizing the pulse width and maximizing the NA may not be the most direct route to inducing high magnitude phase change in hydrogels. The only samples which did not experience damage at high laser powers were those which used a long pulse width, greater than 300 fs. By combining varying pulse widths with a lower effective NA, phase change in excess of 2 waves at 633 nm was seen for the first time (FIG. 25).

LIRIC is a multiphoton process which depends directly on peak power in the focal volume. Therefore, high NA and short pulse widths were originally thought to be the best path forward for the process. However, the damage mechanism of LIRIC is not entirely understood. By lengthening the pulse width and increasing the interaction area by decreasing the NA, the laser damage threshold was pushed to higher powers, allowing for more induced phase change (FIG. 27).

In the second DOE, DIC microscopy revealed differences in the appearance of laser damage between phase carpets written at different NAs (FIG. 29). The higher NA damage appeared to be carbonization, beginning in the central region and propagating to the ends of the phase bar as power increased. Lower NA writing damage appeared as discrete points that covered the whole phase bar and progressively became more populous as laser power increased. In cases of severe damage at low NA, the whole phase bar appeared covered in these discrete damage points. Femtosecond photo-modification causes thermal, electronic, and chemical reactions within materials. In System 3, the repetition rate was 80 MHz, placing LIRIC in the high repetition rate regime of femtosecond photo-modification. Thermal accumulation may significantly impact the material, as the time between pulses is shorter than the diffusion time of the material. A larger, more diffuse spot size may lower the impact of thermal accumulation, as the laser interaction region is larger. In addition, defects or impurities in the sample would be adversely affected by the laser beam before the bulk material at low NA. With the high NA, high repletion rate writing, thermal effects may dominate, leading to carbonization of material above the damage threshold.

As with the flexure system, System 3 was capable of inducing large magnitudes of phase change over a wide range of input variables. The dynamic range of System 3 was the largest yet due to the scanning system's increased range of scan speeds. The overall dynamic range of the system was largely dependent on the effective NA, with the lowest NA having the largest dynamic range (FIG. 28). The ability to induce clinically-relevant magnitudes of phase change at different scan speeds made System 3 a very flexible system. For example, System 3 achieved 1 wave @ 633 nm using NA=0.19, a scan speed of 800 mm/s, and 0.5 µm lines spacing. In order to inscribe a LIRIC pattern over a 6.5 mm zone with a 0.5 µm linespacing, 13,000 GRIN lines are required. Taking into account that stitching zones are 1 mm in length and that 6 stitching zones will be needed, an 800 mm/s scan speed will require 97.5 s of writing time. This does not include the galvanometer turnaround time or the linear translation of the microscope objective between stitching zones. Regardless, a total time of less than two minutes for a LIRIC refractive corrector is clinically feasible. Furthermore, it may be possible to increase the average laser power and line spacing and still achieve 1 wave of phase change at 633 nm. This will reduce the writing time by a factor of 0.71.

The full factorial DOE on System 3 laid the foundations for a hydrogel nomogram. Most specifically, the relationship between fill factor and induced phase change at a given power allowed the nomogram to combine two variable parameters into one FIG. 30. The DOE demonstrated the interaction between NA and line spacing could be tailored alongside scan speed to maximize phase change while minimizing LIRIC procedure time.

The preliminary investigation of linear polarization states revealed no significant impact on the magnitude of LIRIC photo-modification. The induced phase change was nearly identical for the two linear polarization states. Hydrogel material is isotropic; therefore, the insignificance of linear polarization was expected.

Finally, an investigation into the time-dependent increase in induced phase change revealed several possible solutions for long-term stability in hydrogel polymer materials such as Contamac 58. Monitoring of phase carpets showed continued increases in phase change for up to 100 or more days. It was believed this increase was due to water diffusing into the laser-treated area slowly over time. All phase carpets were writing at ~250 µm below the surface of 500 µm thick Contamac 58 buttons. The diffusion process is mediated by the thickness and diffusivity of the sample. The experiments were designed to increase diffusion by swelling the material, either by soaking in a new media or through the application of intense heat and pressure. In addition, swelling of the material would allow loose monomers or n-mers created by the LIRIC process to escape, leaving behind small voids in the polymer structure, allowing increased water content in those areas. This process of flushing out loose monomers from the laser-treated area to be replaced by water would cause an increase in induced phase change. In case of distilled water, it was clear that the swelling of the material greatly expedited the stabilization of induced phase. The same was true of the sample processed by the autoclave. While the final, stable magnitude of induced phase change was similar to the control sample, the autoclave sample was processed much sooner than the others. The sample was processed one day after LIRIC writing and had no time for "natural" time dependent phase change increase, whereas the distilled water and PuriLens sample had been resting in a saline solution for 35 days before being moved to a new storage medium.

One recommendation for long-term stabilization of hydrogel products is a one hour soak in distilled water, followed by the autoclave, and finally storage in PuriLens or another similar commercial contact lens solution. The initial swelling due to water will increase the magnitude of phase change to its hypothetical maximum, the autoclave will immediately stabilize the phase change while sterilizing the product, and PuriLens maintains phase change stability over time.

Previous LIRIC systems generally concentrated on maximizing NA and minimizing pulse width. However, the results from a 12 sample full factorial DOE showed that longer pulse widths and lower NAs produced higher magnitudes of phase change before damage. In fact, the laser damage threshold was significantly increased by lengthening the pulse, allowing more laser power to be deposited. The galvanometer scanning system drastically increased the dynamic range of LIRIC by modulating fill factor and speed simultaneous. The results of the System 3 DOE suggested that clinically relevant LIRIC patterns can be written at high speeds by maximizing the fill factor.

Using the information derived from the experiments discussed above, including information about the maximum phase shift obtainable in a given material at applicable scanning speeds, numerical apertures, and pulse widths, commercial scale LIRIC systems and methods with enhanced efficiencies can be designed and implemented. More particularly, laser damage thresholds and induced phase change ranges may be optimizing in a method of writing LIRIC phase change structures in a hydrogel material, by selecting a laser pulse width and an effective laser NA for a given laser average power range to increase the laser damage threshold relative to use of laser pulse widths shorter than the selected laser pulse width and and/or use of laser NAs greater than the selected laser NA.

In particular embodiments, e.g., when writing in hydrogel materials with an average focused laser power per writing of between 1 mW and 5,000 mW, e.g., it has been found advantageous to operate with a laser pulse width of greater than or equal to about 165 fs (more particularly greater than or equal to each of about 180 fs, about 200 fs, about 210 fs, about 250 fs, about 300 fs, or about 350 fs), in combination with an effective NA of less than or equal to about 0.50 (more particularly less than or equal to each of about 0.49, about 0.4, about 0.3, about 0.26, about 0.25, about 0.2, or about 0.19). While such combination of selected pulse widths and effective NAs represent relatively longer pulse widths and smaller NA than typically employed in prior disclosed LIRIC examples for such average focused laser power, in further specific embodiments pulse widths still preferably may be maintained to less than or equal to about 1000 fs, less than or equal to about 500 fs, or less than or equal to about 400 fs, and the effective NA be maintained to greater than or equal to about 0.05 or greater than or equal to about 0.1, in order to achieve effective LIRIC performance.

In various embodiments, one or more of the following additional features may further be employed alone or in combination: the focused, visible or near-IR laser has a pulse energy from 0.01 nJ to 1000 nJ; a multiple-photon-absorbing chromophore may be incorporated into the optical polymeric materials prior to modifying the refractive index of the optical polymeric materials; locations defined by the focus spot are selected to form a structure selected from the group consisting of Bragg gratings, arbitrary wavefronts, microlens arrays, zone plates, and Fresnel lenses; the laser pulses are emitted at a frequency between 1 MHz and 1000 MHz; the laser pulses have an average focused power per writing head between 1 mW and 5,000 mW; the laser pulses have a focused pulse energy between 1 and 1000 nJ; the size of the focus spot is between 0.5 micrometer and 2 micrometer; the focus spot is scanned at a scanning speed of at least 1 mm/s; the focus spot is scanned at a scanning speed of at least 100 mm/s; the focus spot is scanned at a scanning speed of at least 1 m/s; the laser pulses have a wavelength between 400 and 1,500 nm; the wavelength is between 700 and 900 nm; the laser pulses have a wavelength between 1,000 and 1,300 nm; the laser pulses have a wavelength between 350 and 600 nm; the laser pulses have a wavelength between 400 and 700 nm; the laser pulses have a wavelength between about 400 and 405 nm.

The methods and apparatus described above can be used to modify the refractive index of an intraocular lens following the surgical implantation of the intraocular lens in a human eye, or before the lens is implanted in an eye. Similarly, contact lenses and corneal inlays may also be altered before or after implant or application to an eye.

Optical, hydrogel polymeric materials that can be irradiated with a laser according to the methods described to form refractive correctors in accordance with various embodiments can be any optical, hydrogel polymeric material known to those of ordinary skill in the polymeric lens art, particularly those in the art familiar with optical polymeric materials used to make intraocular lenses or contact lenses. Broadly, non-limiting examples of such materials include those used in the manufacture of ophthalmic devices, such as siloxy-containing polymers, acrylic, hydrophilic or hydrophobic polymers or copolymers thereof-even though some of these hydrophobic materials may not typically be called hydrogels, they are included here and LIRIC applies to such materials similarly, even if the refractive index changes may be different or less. The forming of the refractive structures is particularly suited for modifying the refractive index in select and distinct regions of a polymeric, optical silicone hydrogel, or a polymeric, optical non-silicone hydrogel. Contaflex GM Advance 58 (Contamac Inc.), employed in examples discussed above, e.g., is made of "Acofilcon A", a synonym for 2-Butenedioic acid (2Z)—, di-2-propenyl ester, polymer with 2,3-Dihydroxypropyl 2-methyl-2-propenoate, 1-Ethenyl-2-pyrrolidinone, 2-Hydroxyethyl 2-methyl-2-propenoate and Methyl 2-methyl-2-propenoate.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will preferably have a relatively high refractive index of approximately 1.40 or greater, particularly 1.48 or greater. Many of these materials are also characterized by a relatively high elongation of approximately 80 percent or greater.

Various lasers may be used for the writing system. Non-limiting examples include pulsed femtosecond lasers (such as lasers with a pulsewidth less than 1000 fs and a repetition rate in the range of 1 to 1000 MHz), operating in the range of 340 nm to 1100 nm (e.g. near 405 nm, 517 nm, 800 nm, or 1035 nm). In certain embodiments, average laser power may be selected to provide average power range of from 1 to 1000 mW (or higher) per writing head. Where excess power is available, the laser beam may be divided to power multiple writing heads.

Any suitable scanning systems may be utilized, including, without limitation, high speed XYZ translation stages, high speed galvanometer scanning systems, and shaker scanners (such as described in U.S. Patent Application Publication No. 2016/0144580 published May 26, 2016 to Wayne H., Knox et al.). In some instances, the scanning speed may be in the range of 1 mm/sec to 10 meters/sec, or higher.

The scanning and delivery subsystem may deliver short laser pulses of sufficient energy (e.g. above a minimal threshold but below a damage threshold) and at sufficient scan speeds (e.g. above a damage threshold but below an upper speed threshold) to cause a nonlinear absorption of photons (typically multi-photon absorption), leading to a change in the refractive index of the material at the focus point. The damage threshold may reflect a threshold in which a degradation in optical quality of the device is detectable. Moreover, the region of the material just outside the focal region is minimally affected by the laser light. Accordingly, select regions of an optical, polymeric material can be modified with a laser resulting in a change in the refractive index in these regions. The irradiated regions may exhibit no significant differences in the Raman spectrum with respect to the non-irradiated regions. Also, the irradiated regions may exhibit little or no scattering loss, which means that the structures formed in the irradiated regions are not clearly visible under appropriate magnification without contrast enhancement.

The writing system may be utilized to create lenses or other optical constructs in the interior of the material. Depending on the maximum phase shift required, the lens or other optical construct can be written into the material in a single layer or in multiple layers. U.S. Pat. No. 8,932,352, issued Jan. 13, 2015 to Wayne H. Knox et al. for an "Optical Material and Method for Modifying the Refractive Index" and U.S. Pat. No. 9,144,491, issued Sep. 29, 2015 to Wayne H. Knox et al. for a "Method for Modifying the Refractive Index of an Optical Material," describe additional examples of gratings and other optical constructs that may be written into materials.

The example results discussed herein and suggested combinations of pulse width and effective NA in a LIRIC system may be further employed in combination with the methods and systems for scalable manufacturing as discussed in WO2020/102514, the disclosure of which is incorporated by reference herein, for modifying a plurality of ophthalmic devices with a laser powering a plurality of laser writing heads.

The invention claimed is:

1. A method for optimizing laser damage threshold and induced phase change range in a method of writing phase change structures in a hydrogel material with a femtosecond laser writing system focusing a laser beam into the hydrogel material, comprising selecting a laser pulse width and a laser effective NA for a given focused laser average power range to increase the laser damage threshold and induced phase change range relative to use of laser pulse widths shorter than the selected laser pulse width and/or use of laser effective NAs greater than the selected laser effective NA, wherein the focused laser average power is from 1 to 5000 mW, the selected laser pulse width is greater than about 165 fs, and the selected laser effective NA is less than 0.50.

2. The method of claim 1, wherein the selected laser pulse width is greater than or equal to about 180 fs.

3. The method of claim 1, wherein the selected laser pulse width is greater than or equal to about 210 fs.

4. The method of claim 1, wherein the selected laser pulse width is greater than or equal to about 250 fs.

5. The method of claim 1, wherein the selected laser pulse width is greater than or equal to about 350 fs.

6. The method of claim 1, wherein the selected laser pulse width is less than or equal to about 500 fs.

7. The method of claim 6, wherein the selected laser pulse width is less than or equal to about 400 fs.

8. The method of claim 1, wherein the selected laser effective NA is less than or equal to about 0.4.

9. The method of claim 1, wherein the selected laser effective NA is less than or equal to about 0.26.

10. The method of claim 1, wherein the selected laser effective NA is less than or equal to about 0.20.

11. The method of claim 1, wherein the selected laser effective NA is less than or equal to about 0.19.

12. The method of claim 1, wherein the selected laser effective NA is greater than or equal to about 0.05.

13. The method of claim 1, wherein the selected laser effective NA is greater than or equal to about 0.1.

14. The method of claim 1, wherein the focused laser has a wavelength in the visible or near-IR range.

15. A method according to claim 1, further comprising writing a desired phase change pattern in a hydrogel material with the femtosecond laser writing system at the selected laser pulse width and selected laser effective NA for the given focused laser average power range by scanning the pulsed focused laser beam relative to the hydrogel material to write one or more refractive index changes into the hydrogel material.

16. A laser writing system for modifying a hydrogel material, the laser writing system comprising: a laser configured to generate a laser beam; and a laser writing head configured to focus and direct the laser beam to the hydrogel material to write one or more localized refractive index modifications into the hydrogel material; wherein the laser writing system is configured to have a focused laser average power of from 1 to 5000 mW, a laser pulse width of greater than about 165 fs, and a laser effective NA of less than 0.50, wherein the laser pulse width and laser effective NA have been selected in accordance with the method of claim 1.

17. The system of claim 16, wherein the laser is configured to generate a pulsed laser beam having a wavelength in the range of 515 nm to 520 nm, or 1030 nm to 1040 nm, or 400 nm to 410 nm, or 800 nm to 810 nm.

18. The system of claim 16, wherein the hydrogel material is an ophthalmic device selected from contact lenses, intraocular lenses, or corneal implants.

19. The method of claim 1, wherein the selected laser pulse width is less than or equal to about 500 fs and the selected laser effective NA is greater than or equal to about 0.05.

* * * * *